US010012591B2

(12) United States Patent
Notingher et al.

(10) Patent No.: US 10,012,591 B2
(45) Date of Patent: Jul. 3, 2018

(54) MEASUREMENT OF TISSUE STRUCTURES

(71) Applicants: The University of Nottingham, Nottingham (GB); Royal Holloway University of London, Egham (GB)

(72) Inventors: Ioan Notingher, Nottingham (GB); Kenny Kong, Nottingham (GB); Christopher Rowlands, Nottingham (GB); Hywel Williams, Nottingham (GB); Iain Leach, Nottingham (GB); Sandeep Varma, Nottingham (GB); William Perkins, Nottingham (GB); Alexey Koloydenko, Egham (GB)

(73) Assignees: The University of Nottingham, Nottingham (GB); Royal Holloway University of London, Egham (GB)

(*) Notice: Subject to any disclaimer, the term of this patent is extended or adjusted under 35 U.S.C. 154(b) by 196 days.

(21) Appl. No.: 14/778,546

(22) PCT Filed: Mar. 21, 2014

(86) PCT No.: PCT/GB2014/050894
§ 371 (c)(1),
(2) Date: Sep. 18, 2015

(87) PCT Pub. No.: WO2014/147416
PCT Pub. Date: Sep. 25, 2014

(65) Prior Publication Data
US 2016/0290926 A1    Oct. 6, 2016

(30) Foreign Application Priority Data
Mar. 21, 2013  (GB) .................................. 1305171.9

(51) Int. Cl.
*G01N 21/64*  (2006.01)
*G01N 21/65*  (2006.01)
(Continued)

(52) U.S. Cl.
CPC .......... *G01N 21/6486* (2013.01); *G01J 3/027* (2013.01); *G01J 3/28* (2013.01);
(Continued)

(58) Field of Classification Search
None
See application file for complete search history.

(56) References Cited

U.S. PATENT DOCUMENTS 7,359,815 B2    4/2008  Pirzer et al.
7,956,996 B2 *  6/2011  Maier .................. A61B 5/0059
                                                        356/301
(Continued)

FOREIGN PATENT DOCUMENTS

WO    WO-2010/131045 A1    11/2010
WO    WO 2010131045 A1 *   11/2010 ............. G01N 21/65

OTHER PUBLICATIONS

Croucher, J., "International Search Report" for PCT/GB2014/050894 dated Jun. 12, 2014, 3 pages.
(Continued)

*Primary Examiner* — Shawn Decenzo
(74) *Attorney, Agent, or Firm* — Winstead PC

(57) ABSTRACT

The disclosure relates to measurement and classification of tissue structures in samples using a combination of light imaging and spectroscopy, in particular although not necessarily exclusively for detection of tumors such as basal cell carcinoma or breast tumors in tissue samples. Embodiments disclosed include a method of automatically identifying tissue structures in a sample, the method comprising the steps of: measuring (1702, 1703) a response of an area of the sample to illumination with light; identifying (1704) regions within the area having a measured response within a predetermined range; determining (1705) locations within the identified regions; performing (1706) spectroscopic analysis
(Continued)

of the sample at the determined locations; and identifying (1707) a tissue structure for each region from the spectroscopic analysis performed on one or more locations therein.

25 Claims, 17 Drawing Sheets

(51) Int. Cl.
G01N 21/00 (2006.01)
G01J 3/28 (2006.01)
G01N 33/483 (2006.01)
G01N 35/00 (2006.01)
G01J 3/02 (2006.01)

(52) U.S. Cl.
CPC ..... *G01N 21/6408* (2013.01); *G01N 21/6458* (2013.01); *G01N 21/65* (2013.01); *G01N 33/4833* (2013.01); *G01N 35/00* (2013.01); *G01N 2021/6417* (2013.01); *G01N 2201/06113* (2013.01); *G01N 2800/7028* (2013.01)

(56) References Cited

U.S. PATENT DOCUMENTS

| | | | | |
|---|---|---|---|---|
| 2004/0010197 | A1* | 1/2004 | Faupel | A61B 5/0071 600/476 |
| 2012/0078524 | A1* | 3/2012 | Stewart | A61B 5/0059 702/19 |

OTHER PUBLICATIONS

Mohs, Frederic E., *Chemosurgery: A Microscopically Controlled Method of Cancer Excision.* Arch Surg, 1941. 42(2): p. 279-295.
Mosterd, K., et al., *Surgical excision versus Mohs' micrographic surgery for primary and recurrent basal cell carcinoma of the face: a prospective randomised controlled trial with 5 years' follow up.* Lancet Oncology, 2008. 9(12): p. 1149-1156.
Mogensen, M. et al., *Diagnosis of nonmelanoma skin cancer/keratinocyte carcinoma: A review of diagnostic accuracy of nonmelanoma skin cancer diagnostic tests and technologies.* Dermatologic Surgery, 2007. 33(10): p. 1158-1174.
Raab, S.S. et al., *Quality in Cancer Diagnosis.* CaDa Cancer Journal for Clinicians, 2010. 60(3): p. 139-165.
Nijssen, A., et al., *Discriminating Basal Cell Carcinoma from its Surrounding Tissue by Raman Spectroscopy.* Journal of Investigative Dermatology, 2002. 119(1): p. 64-69.
Lieber, C.A., et al., *In Vivo Nonmelanoma Skin Cancer Diagnosis Using Raman Microspectroscopy.* Lasers in Surgery and Medicine, 2008. 40(7): p. 461-467.
Gniadecka, M., et al., *Diagnosis of Basal Cell Carcinoma by Raman Spectroscopy.* Journal of Raman Spectroscopy, 1997. 28(2-3): p. 125-129.
Larraona-Puy, M., et al., *Development of Raman microspectroscopy for automated detection and imaging of basal cell carcinoma.* Journal of biomedical optics, 2009. 14(5): p. 054031-1-054031-10.
Larraona-Puy, M., et al., *Discrimination between basal cell carcinoma and hair follicles in skin tissue sections by Raman micro spectroscopy.* Journal of Molecular Structure, 2011. 993(1-3): p. 57-61.
Almond, L.M., et al., *Raman spectroscopy: a potential tool for early objective diagnosis of neoplasia in the oesophagus.* Journal of Biophotonics, 2011. 4(10): p. 685-695.
Tollefson, M., et al., *Raman spectral imaging of prostate cancer: can Raman molecular imaging be used to augment standard histopathology?* Bju International, 2010. 106(4): p. 484-488.

Haka, A.S., et al., *Diagnosing breast cancer by using Raman spectroscopy.* Proceedings of the National Academy of Sciences of the United States of America, 2005. 102(35): p. 12371-12376.
McIntosh, L.M., et al., *Towards Non-Invasive Screening of Skin Lesions by Near-Infrared Spectroscopy.* Journal of Investigative Dermatology, 2001. 116(1): p. 175-181.
Bird, B., et al., *Infrared spectral histopathology (SHP): a novel diagnostic tool for the accurate classification of lung cancer.* Laboratory Investigation, 2012. 92(9): p. 1358-1373.
Hutchings, J., et al., *The potential for histological screening using a combination of rapid Raman mapping and principal component analysis.* Journal of Biophotonics, 2009. 2(1-2): p. 91-103.
Rowlands, C.J., et al., *Rapid acquisition of Raman spectral maps through minimal sampling: applications in tissue imaging.* Journal of Biophotonics, 2012. 5(3): p. 220-229.
Begin, S., et al., *Coherent anti-Stokes Raman scattering hyperspectral tissue imaging with a wavelength-swept system.* Biomedical Optics Express, 2011. 2(5): p. 1296-306.
Saar, B.G., et al., *Video Rate Molecular Imaging in Vivo with Stimulated Raman Scattering.* Science, 2010. 330(6009): p. 1368-1370.
Tu, A.T., *Raman Spectroscopy in Biology: Principles and Applications.* 1982: Wiley-Blackwell.
Movasaghi, Z. et al., *Raman Spectroscopy of Biological Tissues.* Applied Spectroscopy Reviews, 2007. 42(5): p. 493-541.
Okuno, M. et al., *Multifocus confocal Raman microspectroscopy for fast multimode vibrational imaging of living cells.* Optics Letters, 2010. 35(24): p. 4096-4098.
Wartewig, S., *IR and Raman Spectroscopy: Fundamental Processing.* 2003: Wiley-VCH.
Duda, R.O. et al., *Pattern Classification, 2nd Edition.* 2001: Wiley & Sons, Inc.
Ly, E., et al., *Differential diagnosis of cutaneous carcinomas by infrared spectral micro-imaging combined with pattern recognition.* Analyst, 2009. 134(6): p. 1208-1214.
Sebiskveradze, D., et al., *Automation of an algorithm based on fuzzy clustering for analyzing tumoral heterogeneity in human skin carcinoma tissue sections.* Laboratory Investigation, 2011. 91(5): p. 799-811.
O'Callaghan, R.J. et al., *Combined Morphological-Spectral Unsupervised Image Segmentation.* IEEE Transactions on Image Processing, 2005. 14(1): p. 49-62.
Lin, K. et al., *Integrated autofluorescence endoscopic imaging and point-wise spectroscopy for real-time in vivo tissue measurements.* JBO Letters vol. 15(4) 2010, 040507-1-040507-3.
Bergholt, M.S. et al, *Combining near-infrared-excited auto fluorescence and Raman spectroscopy improves in vivo diagnosis of gastric cancer,* Biosensors and Bioelectronics, 2011 (26): p. 4104-4110.
Bennet, N., *One in five need reoperation after breast-conserving surgery.* The Lancet Oncology, 2012. 13:e334.
Huang, Z. et al., *Integrated Raman spectroscopy and trimodal wide-field imaging techniques for real-time in vivo tissue Raman measurements at endoscopy.* Optics Letters, 2009. 34(6): p. 758-760.
Rowlands, C.J. et al., *Rapid acquisition of Raman spectral maps through minimal sampling: applications in tissue imaging.* Journal of BioPhotonics, 2012. 5(3): p. 220-229.
Bergholt, M. S., et al., *Characterizing variability in in vivo Raman spectra of different anatomical locations in the upper gastrointestinal tract toward cancer detection.* Journal of Biomedical Optics, 2011. 16(22): p. 037003-1-037003-10.
Fenn, M. B., et al., *Raman Spectroscopy for Clinical Oncology.* Advances in Optical Technologies, 2011. 213783: p. 1-20.

* cited by examiner

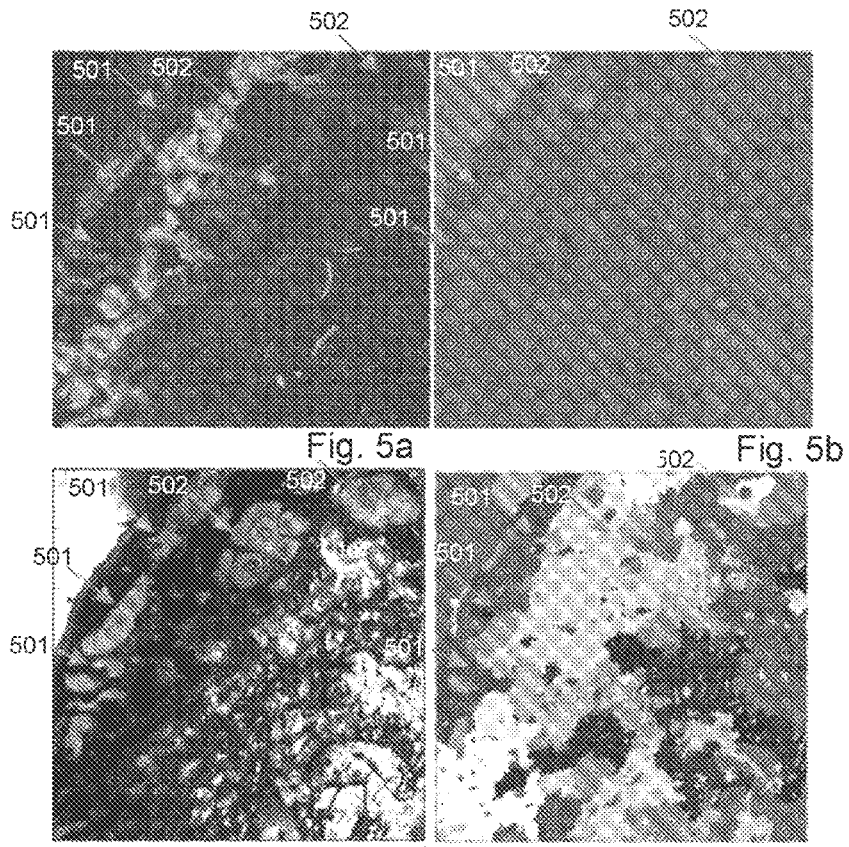
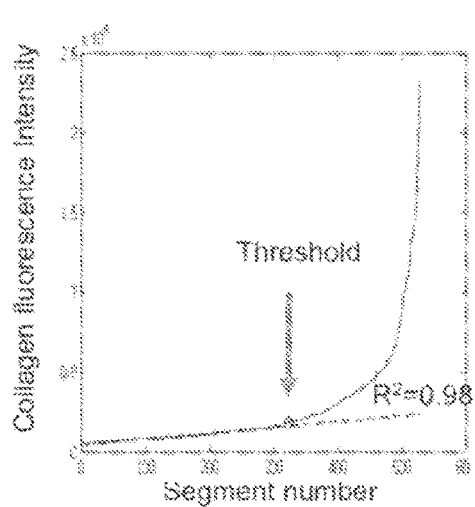 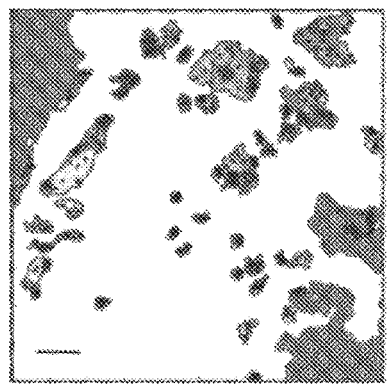
Fig. 5e  Fig. 5f

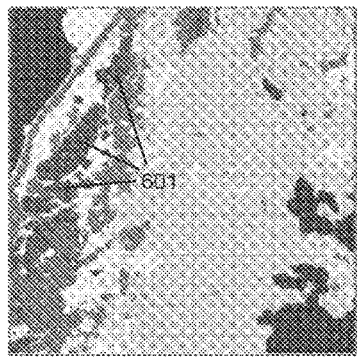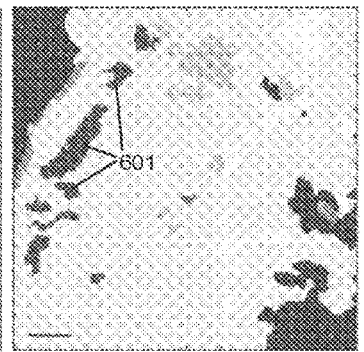
Fig. 6a  Fig. 6b
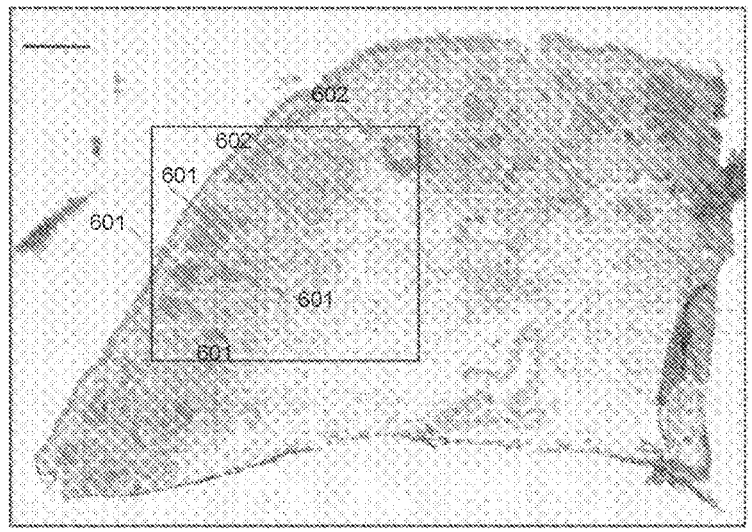
Fig 6c

BCC M OGl Fat D In.D Ep. Unk.

BCC M OGl Fat D In.D Ep. Unk.

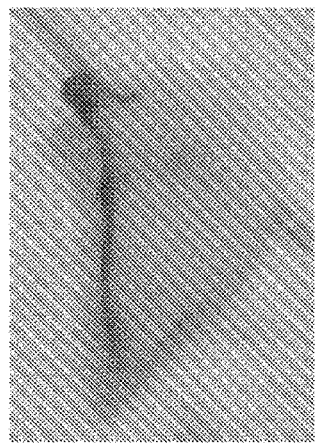  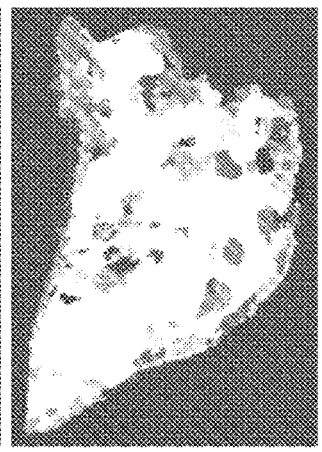
Fig. 14a　　　Fig. 14b　　　Fig. 14c
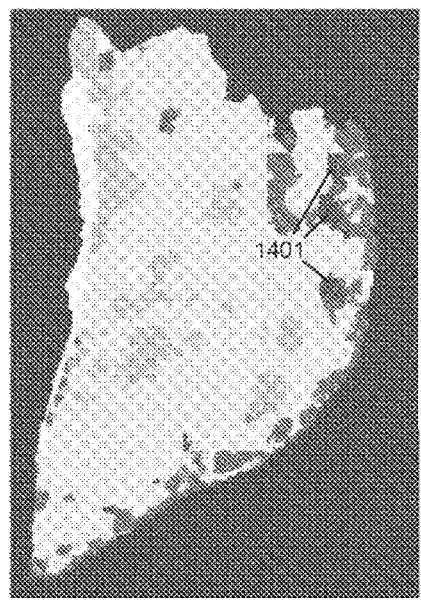 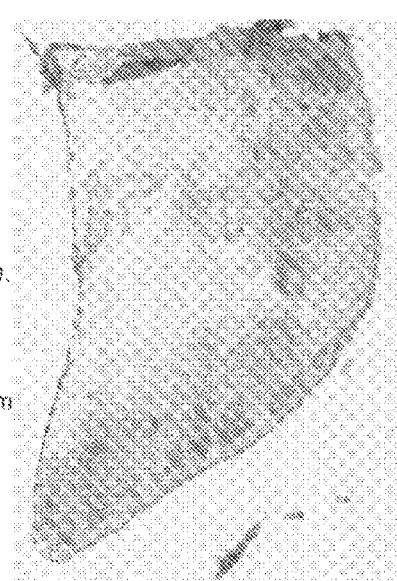
- BCC
- Muscle
- Fat
- Dermis
- Inflamed D.
- Epidermis
- Substrate
- Dye contam
Fig. 14d　　　Fig. 14e

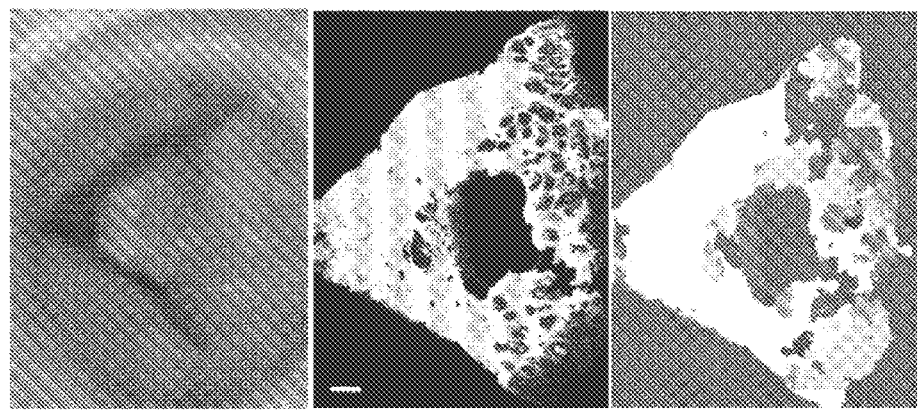
Fig. 15a  Fig. 15b  Fig. 15c
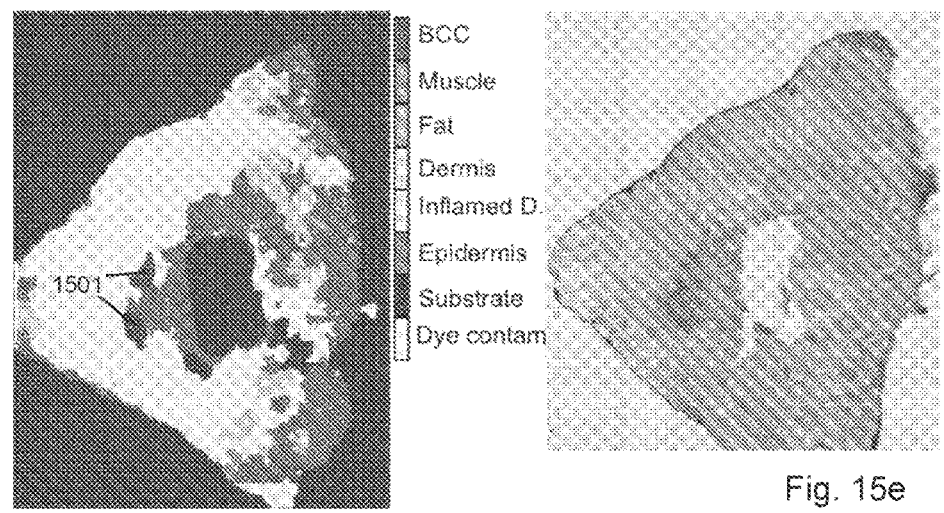
Fig. 15d
Fig. 15e

MEASUREMENT OF TISSUE STRUCTURES

FIELD OF THE INVENTION

The invention relates to measurement and classification of tissue structures in samples using a combination of light imaging and spectroscopy, in particular although not necessarily exclusively for detection of tumours such as basal cell carcinoma or breast tumours in tissue samples.

BACKGROUND

In tissue-conserving surgery sequential layers of tissues are excised to ensure the removal of all tumour cells while maintaining as much healthy tissue as possible. Negative margins (in which all cancerous cells are removed) have been directly associated with lower local recurrence rates in many cancer types. Conservation of healthy tissue is important for tissue function preservation, wound healing and cosmesis. However, identifying the tumour margins intra-operatively remains one of the key challenges in tissue-conserving surgery.

Histopathology is generally considered to be the "gold standard" method for evaluation of tissues for many diseases, including cancer. This involves staining of thin tissue sections (thickness ~10 µm) with various contrast enhancing chemicals followed by examination under an optical microscope, which allows the discrimination of tissue structures and identification of any tumours. Histopathology is an invaluable tool for evaluating the tumour resection margins during tissue-conserving surgery.

Mohs micrographic surgery (MMS) for the treatment of basal cell carcinoma (BCC) relies on the removal of sequential tissue layers, which are evaluated during surgery by frozen section histopathology. If the pathologic evaluation during MMS indicates tumour persistence, the location of the tumour is recorded and further tissue removal is performed by the surgeon. BCC is a major health problem as it accounts for ~75% of skin cancer cases worldwide with more than 60,000 cases being diagnosed each year in the UK. Although BCC rarely spreads to distant sites in the body, these cancers can lead to significant tissue destruction and dysfunction. Some BCCs have higher risks of recurrence (43% for regions near the eye and 33% for superior orbital rim and brow), which lead to more aggressive recurrent BCCs. If the treatment option were selected based on lowest recurrence rate, it has been argued that MMS would be chosen for every BCC (Arch Dermatol 1999; 135(10): 1255; Brit J Dermatol 1999; 141(3): 415). It has been shown that the 5-year recurrence rates for BCC treated by MMS are 1.4%-2.5% for primary and 2.4%-4% for recurrent BCC, significantly lower than for standard excision (3.2%-10% for primary and 12.1%-17% for recurrent BCC). However, the high costs have limited the availability of MMS throughout the UK, leading to an inequitable health service provision. In 2006 NICE (the UK National Institute for Health and Clinical Excellence) recommended that every specialist skin cancer team should be equipped with MMS for treating BCC. This is not the case at present due to limited availability of histopathology technicians skilled in frozen section preparation and skilled surgeons. Failure to provide MMS for difficult cases of BCC results in additional surgery for removal of recurrent tumours, causing additional morbidity for BCC sufferers and deferred costs to the NHS.

In many cases, the traditional methods of histopathological examination of resection specimens require tissue preparation procedures which, for practical reasons, cannot be performed intra-operatively. For example, breast conserving surgery (BCS) relies on visual or X-ray inspection of excised tissues, techniques which have significantly lower diagnosis accuracy compared to histopathology. Breast cancer is the most common type of cancer for women (45,000 new patients per year in the UK) and approximately 58% of the patients have BCS as their first treatment option. However, a recent retrospective study showed that 20% of patients in England treated by BCS between 2005 & 2008 required a secondary surgery (The Lancet Oncology 2012, 13:e334). This study highlights the low accuracy of the current methods used for intra-operative diagnosis. Secondary surgery has numerous negative consequences, including delaying adjuvant treatment, poorer aesthetic outcomes, longer recovery times, emotional stress to patients and increased costs to the healthcare services. The increased healthcare costs associated with secondary surgery represents a huge challenge to the healthcare service, especially when considering the current plans in the UK to expand the screening program to women younger than 50. Such expansions will lead to an increased number of patients with early stage breast tumours, for whom BCS is generally the most appropriate treatment.

Recently, Raman spectroscopy has emerged as a powerful technique for the diagnosis of cancers and imaging of tumours. Raman hand-held probes based on fibre optics have already been proposed for intra-operative evaluation of tumour margins (PNAS 2005; 102(35): 12371) as well as for guided biopsy (Opt Lett 2009; 34(6): 758). However, these methods allow only single-point measurements, which lack the spatial accuracy to detect small tumours. Spectral imaging based on Raman microscopic techniques has the advantage of containing both the morphological and chemical information at a high spatial resolution suitable for the detection of small tumours.

Alterations in the molecular properties of tissues during tumour growth provide the additional quantifiable information which can be used for objective diagnosis. Raman microscopy techniques have been used for imaging tumours within thin tissue sections (10-20 µm thickness) and multivariate statistical models had been developed for providing accurate diagnosis (typical sensitivities and specificities higher than 95%) for a wide range of tissues, including skin (J Biomed Opt 2009; 14(5): 054031) and prostate (Bju Int 2010; 106(4): 484). While these studies demonstrated the potential for using Raman microscopy for both imaging and unsupervised diagnosis of tumours, the work reported so far used raster-scanning (or line-scanning), which limited the diagnosis to small tissue areas (below 1 mm) or only single point measurements. Measurements of larger tissue samples at the required spatial resolution of 10-15 µm would require 20-40 hours, which is not practical during surgery. Thus, these methods are not suitable for diagnosis of thick and large tissue samples (1-2 cm) as typically excised during tissue conserving surgery.

It is an object of the invention to address one or more of the above mentioned problems.

SUMMARY OF THE INVENTION

In accordance with the invention there is provided a method of automatically identifying tissue structures in a sample, the method comprising the steps of:
  measuring a response of an area of the sample to illumination with light;
  identifying regions within the area having a measured response within a predetermined range;

determining locations within the identified regions;
performing spectroscopic analysis of the sample at the determined locations; and
identifying a tissue structure for each region from the spectroscopic analysis performed on one or more locations therein.

An advantage of the method is that by first obtaining a light image of the sample area and determining regions within the area, spectroscopic analysis, which typically takes an extended amount of time for each location, can be restricted to only locations that need to be measured to identify specific regions within a sample area. The overall time taken to carry out spectroscopic analysis to determine tissue structures within a sample can thereby be greatly reduced, while retaining accuracy of identification.

The spectroscopic analysis may be performed using vibrational spectroscopy, for example by means of Raman spectroscopy.

The light the sample is illuminated with may be ultraviolet light. The measured response may be a measured value of fluorescence. The measured fluorescence value may for example be a measure of intensity or a measure of fluorescence lifetime. The identified regions may have a measured fluorescence value greater than or less than a predetermined threshold value.

Regions identified within the sample area may have a minimum predetermined size, i.e. regions below the predetermined size may be discounted for spectroscopic analysis. The minimum predetermined size may be a region having a linear extent of greater than around 100 µm, 50 µm, 20 µm or 10 µm, or a region having an area of greater than around 0.01 mm$^2$, 0.0025 mm$^2$, 0.0004 mm$^2$ or 0.0001 mm$^2$.

A particular tissue structure may be identified for each region based on matching a spectrum from spectroscopic analysis of one or more locations within each region from a database of spectra for, or corresponding to, different tissue structures. The different tissue structures may include a tumour such as a breast or skin tumour, and may include a basal cell carconima.

A number of locations are identified within each region dependent on its size. The number of locations may be two or more for each region. The total number of locations, and consequently the total number of spectra obtained during the step of spectroscopic analysis, is preferably 100 or fewer, and may be 500 or fewer, for a single sample having a sample area of 1 mm$^2$ or greater.

One of the identified regions may be identified as a particular tissue structure if two or more spectra from spectroscopic analysis taken at locations within the one of the identified regions indicate the same particular tissue structure. The particular tissue structure may be a basal cell carcinoma or another type of tumour.

One of the identified regions may be identified as a particular tissue structure if a majority, or at least 50%, of spectra from spectroscopic analysis at locations within the one of the identified regions indicate the particular tissue structure.

The locations identified within each region are optionally at least a predetermined distance away from an outer edge of each region. This reduces the possibility of regions being misidentified due to overlap with an adjacent region. The predetermined distance may for example be 10 µm, 20 µm or 50 µm.

In particular embodiments, each region may be identified as dermis, epidermis, basal cell carcinoma or another tissue structure.

According to a second aspect of the invention there is provided an apparatus for automatically identifying tissue structures in a sample, the apparatus comprising:
a sample stage for receiving a sample to be analysed;
a first light source for selectively illuminating an area of the sample;
a first detector for receiving light from the sample upon illumination by the first light source;
a second light source for selectively illuminating a location within the area of the sample; and
a spectral analyser for receiving light from the location within the area of the sample upon illumination by the second light source,
the apparatus being configured to perform a method according to the first aspect of the invention.

The apparatus preferably comprises a computer configured to operate the sample stage, first and second light sources, first detector and spectral analyser. The same computer may also be configured to perform one or more of the steps of identifying regions, determining locations within the identified regions and identifying a tissue structure for each region from the spectroscopic analysis performed on one or more locations therein. One or more of the steps may alternatively be performed by a separate computer.

According to a third aspect of the invention there is provided a computer program comprising instructions for causing a computer to perform the method according to the first aspect. The computer program may be provided on a non-transitory medium such as a non-volatile memory or computer-readable disk.

Disclosed herein is a new optical technique that can be automated and used intra-operatively for objective diagnosis of tissue samples excised during tissue conserving surgery. The new method relies on two complementary techniques to detect chemical differences between tumours and healthy tissue. In particular embodiments, tissue auto-fluorescence (which provides high speed and high sensitivity but low specificity) allows fast evaluation of the main spatial features of tissues and determines the most suitable sampling points for Raman spectroscopy (which provides high sensitivity and specificity but at lower speeds). The potential of this new technique for fast and objective diagnosis of BCC in both tissue sections and un-sectioned tissue layers excised during MMS is demonstrated.

DETAILED DESCRIPTION

Aspects and embodiments of the invention are described in further detail below by way of example and with reference to the enclosed drawings in which.

Figure 7A:
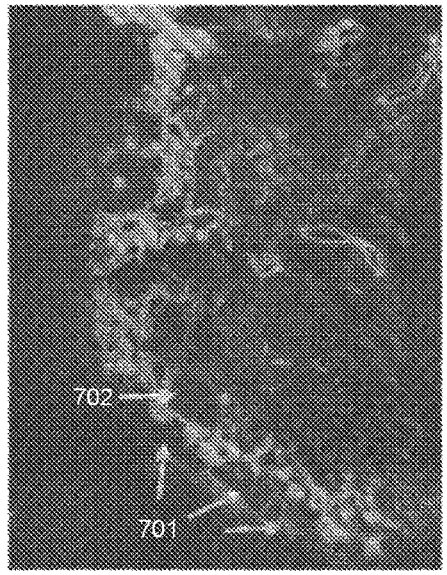
Figure 7B:
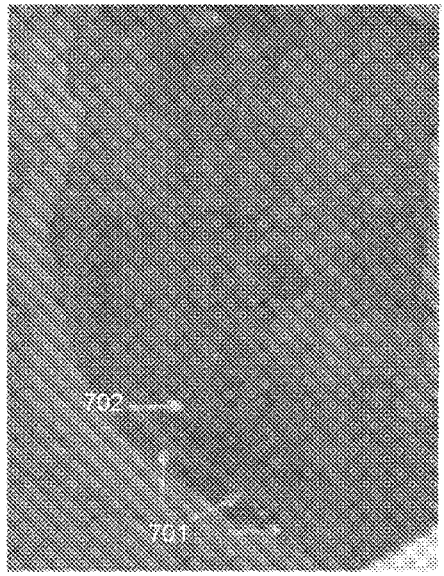
Figure 7C:
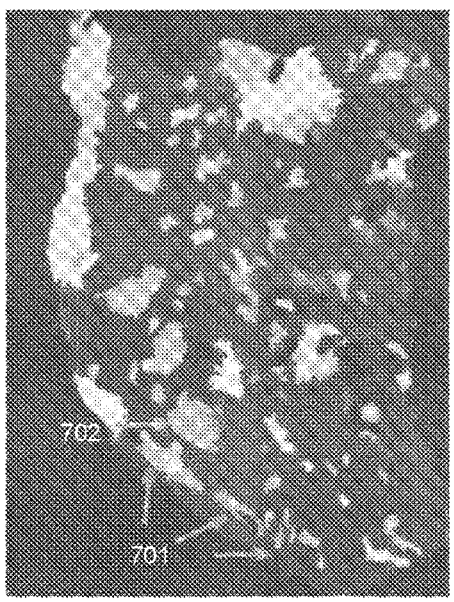
Figure 7D:
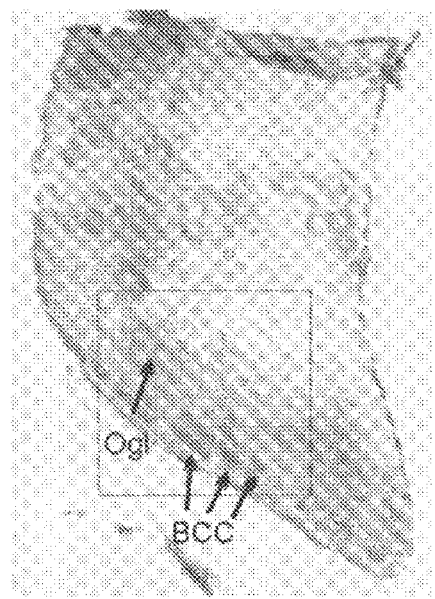
Figure 8:
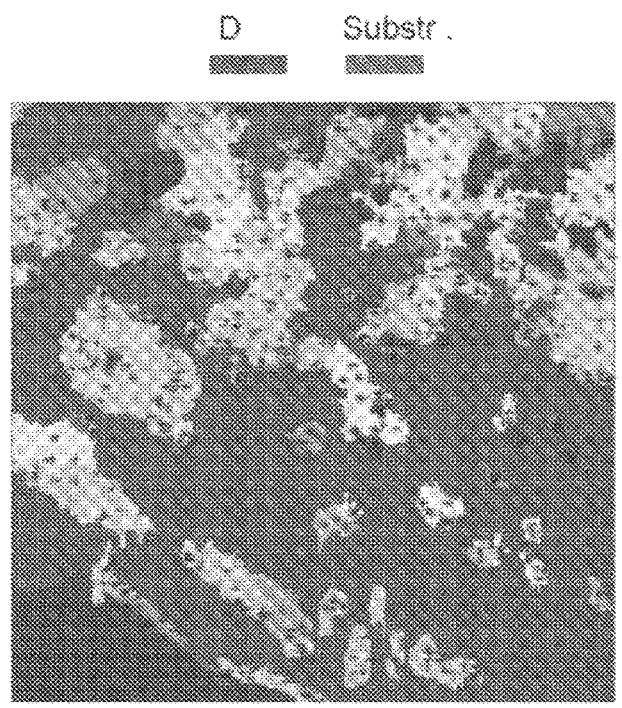
Figure 9A:
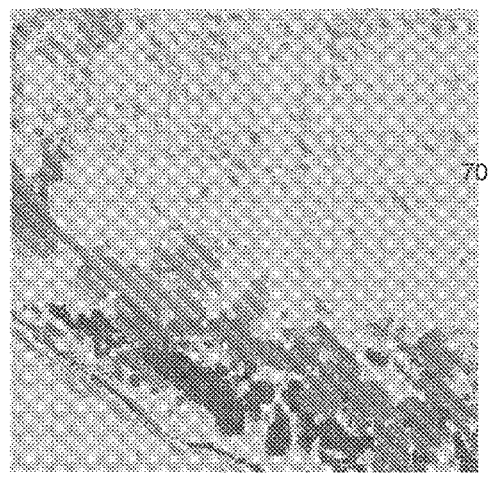
Figure 9B:
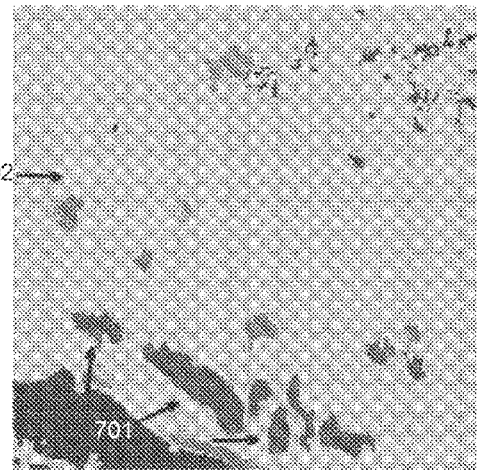
Figure 10A:
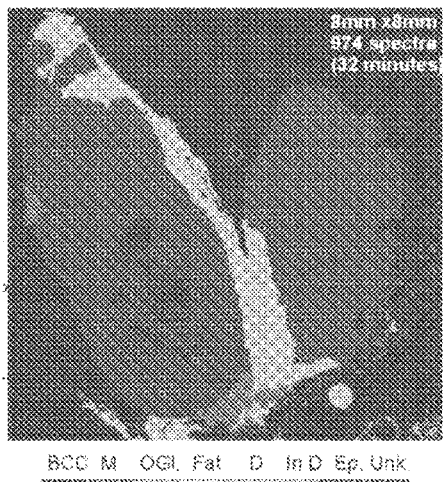
Figure 10B:
Figure 11A:
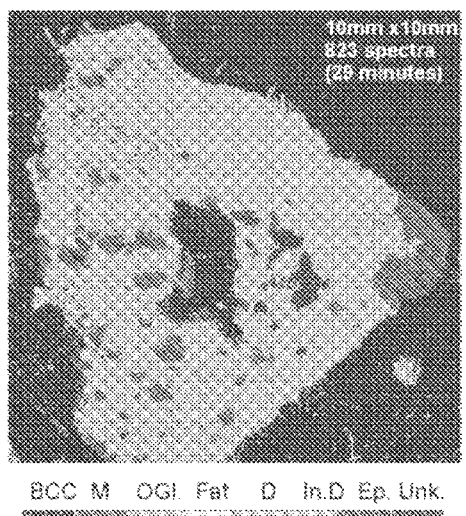
Figure 11B:
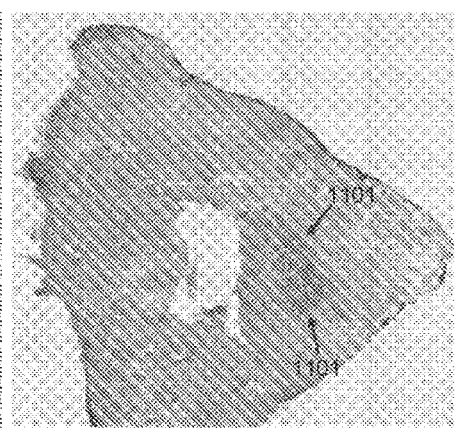
Figure 12A:
Figure 12B:
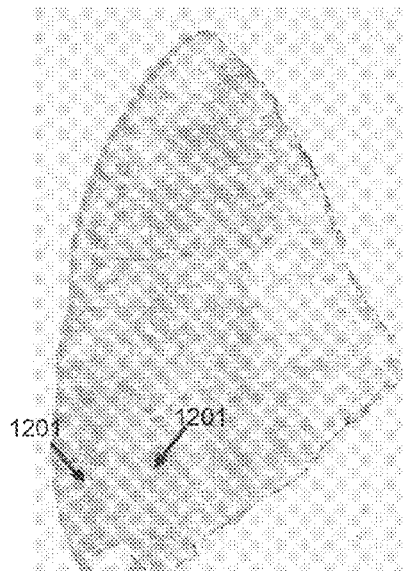
Figure 13A:
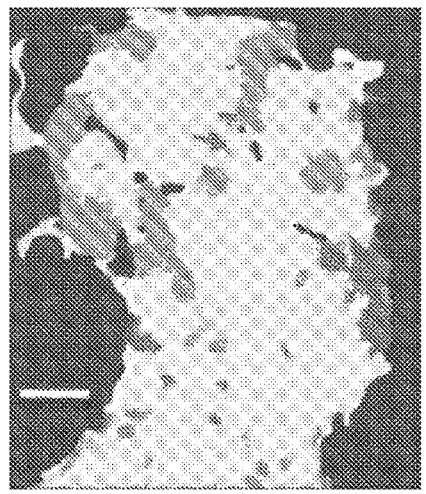
Figure 13B:

FIG. 5a is an autofluorescence intensity image of a sample taken with 377 nm incident light and 447 nm emitted light for indicating the presence of collagen FIG. 5b is an autofluorescence intensity image of the sample of FIG. 5a taken with 292 nm incident light and 357 nm emitted light for indicating the presence of tryptophan FIG. 5c is an image indicating the ratio of intensities corresponding to collagen and tryptophan derived from the images in FIGS. 5a and 5b;

FIG. 5d is a segmented image derived from analysis of the autofluorescence images of FIGS. 5a-5c;

FIG. 5e is a plot of collagen fluorescence intensity as a function of segment number for the image of FIG. 5d, indicating a threshold value;

FIG. 5f is a segmented image derived from FIG. 5d in which segments are removed according to different criteria and locations for spectroscopy are identified;

FIG. 6a is a spectral diagnosis image derived from a raster scan of the sample of FIGS. 5a-5f;

FIG. 6b is a spectral diagnosis image taken from the sample of FIGS. 5a-5f using the sampling points derived and indicated in FIG. 5f (scale bar=0.5 mm);

FIG. 6c is a conventional HE (hematoxylin and eosin) stained histopathology image of an adjacent tissue section to that analysed in FIGS. 5a-5f, indicating regions of BCC tumours and sebaceous glands (scale bar=1 mm);

FIG. 7a is an autofluorescence intensity image of a sample taken with 377 nm incident light and 447 nm emitted light for indicating the presence of collagen;

FIG. 7b is an autofluorescence intensity image of the sample of FIG. 7a taken with 280 nm light and 348 nm emitted light for indicating the presence of tryptophan;

FIG. 7c is a segmented image of the sample of FIGS. 7a and 7b, indicating regions identified according to their autofluorescence intensity;

FIG. 7d is a conventional HE stained histopathology image of an adjacent sample to that of FIGS. 7a-c;

FIG. 8 is an image of a portion of the sample area from FIG. 7c overlaid with markers indicating locations for spectroscopy measurements within the identified regions;

FIG. 9a is an image of the sample area from FIG. 7c taken using a raster scan of Raman spectroscopy measurements across the sample area, identifying regions of different tissue structure;

FIG. 9b is an image of the sample area from FIG. 7c taken using Raman spectroscopy measurements at the locations identified in FIG. 8, with regions of different tissue structure identified according to the regions indicated in FIG. 7c;

FIG. 10a is an image of a sample area of a thin (20 μm) skin section taken according to a method according to the invention, indicating different tissue structures including basal cell carcinoma (BCC);

FIG. 10b is a conventional HE stained histopathology image of an adjacent tissue section to that of FIG. 10a, indicating BCC regions;

FIG. 11a is an image of a further sample area of a skin section taken according to a method according to the invention;

FIG. 11b is a conventional HE stained histopathology image of an adjacent tissue section to that of FIG. 11a;

FIG. 12a is an image of a further sample area of a skin section taken according to a method according to the invention;

FIG. 12b is a conventional HE stained histopathology image of an adjacent tissue section to that of FIG. 12a;

FIG. 13a is an image of a further sample area of a skin section taken according to a method according to the invention;

FIG. 13b is a conventional HE stained histopathology image of an adjacent tissue section to that of FIG. 13a;

FIG. 14a is a visible light image of a thick skin tissue layer sample;

FIG. 14b is an autofluorescence image of the thick skin tissue layer sample of FIG. 10a indicating collagen-containing regions;

FIG. 14c is a spatial correlation map of the sample of FIG. 14a indicating regions according to their autofluorescence intensity;

FIG. 14d is an image of the sample of FIG. 14a with regions having different tissue structures identified by Raman spectroscopy;

FIG. 14e is a conventional HE stained histopathology image of an adjacent section to that of the sample in FIG. 14a;

FIG. 15a is a visible light image of a further thick skin tissue layer sample;

FIG. 15b is an autofluorescence image of the thick skin tissue layer sample of

Figure 16A:
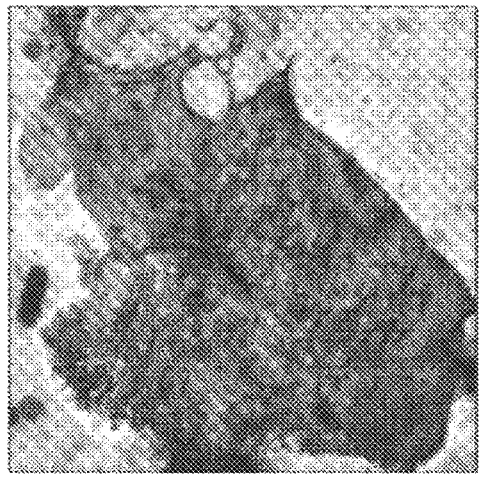
Figure 16B:
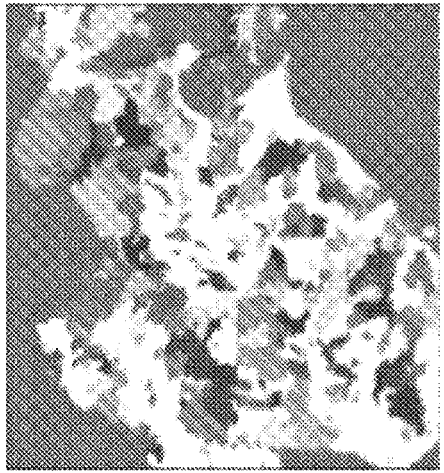
Figure 16C:
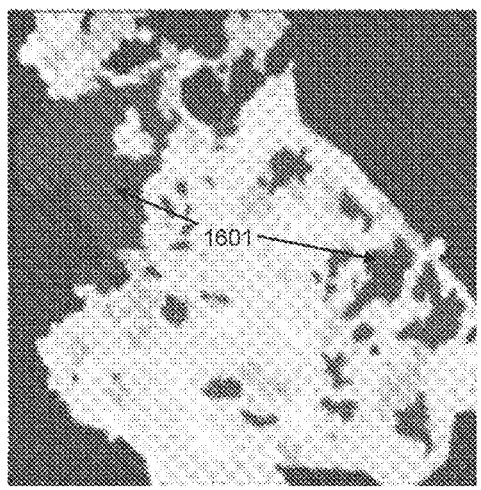
Figure 16D:
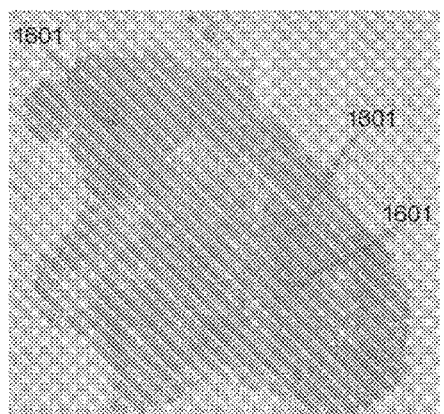
Figure 17:
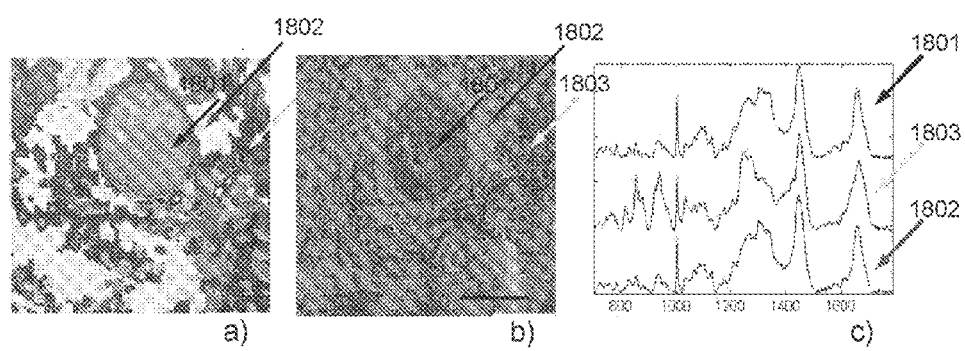
Figure 18:
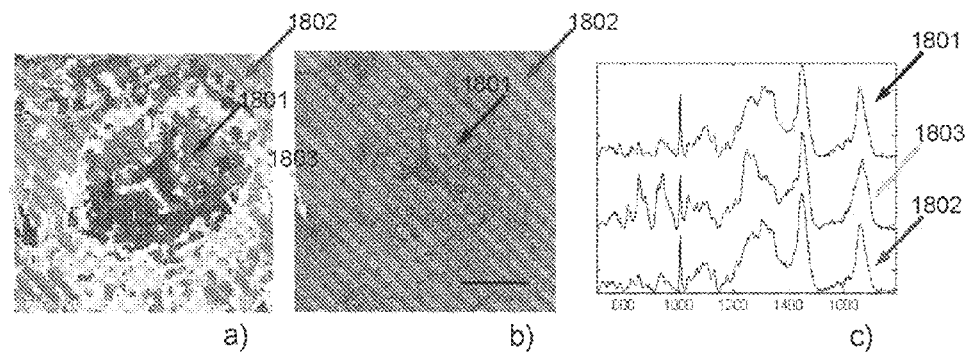

FIG. 15a indicating collagen-containing regions;

FIG. 15c is a spatial correlation map of the sample of FIG. 15a indicating regions according to their autofluorescence intensity;

FIG. 15d is an image of the sample of FIG. 15a with regions having different tissue structures identified by Raman spectroscopy;

FIG. 15e is a conventional HE stained histopathology image of an adjacent section to that of the sample in FIG. 15a;

FIG. 16a is an autofluorescence image of a thin (20 μm) breast tissue sample indicating collagen- and tryptophan-containing regions;

FIG. 16b is a spatial correlation map of the sample of FIG. 16a indicating regions according to their autofluorescence intensity;

FIG. 16c is an image of the sample of FIGS. 16a and 16b with regions having different tissue structures identified by Raman spectroscopy;

FIG. 16d is a conventional HE stained histopathology image of an adjacent section to that of the sample in FIGS. 16a-c;

FIGS. 17 and 18 are examples images and spectra taken from breast tissue (FIG. 17) and ductal carcinoma (FIG. 18) using a two-step k-means clustering algorithm for assigning Raman spectra to structures identified in conventional histopathology sections (scale bar: 300 μm);

FIG. 19a is a diagram of mean Raman spectra of healthy breast tissue structures and tumours: ductal carcinoma (DC-NST), stroma, fat, epithelial cells and stroma containing proliferating tumour cells (Str. Prolif. Cells).

Figure 20:
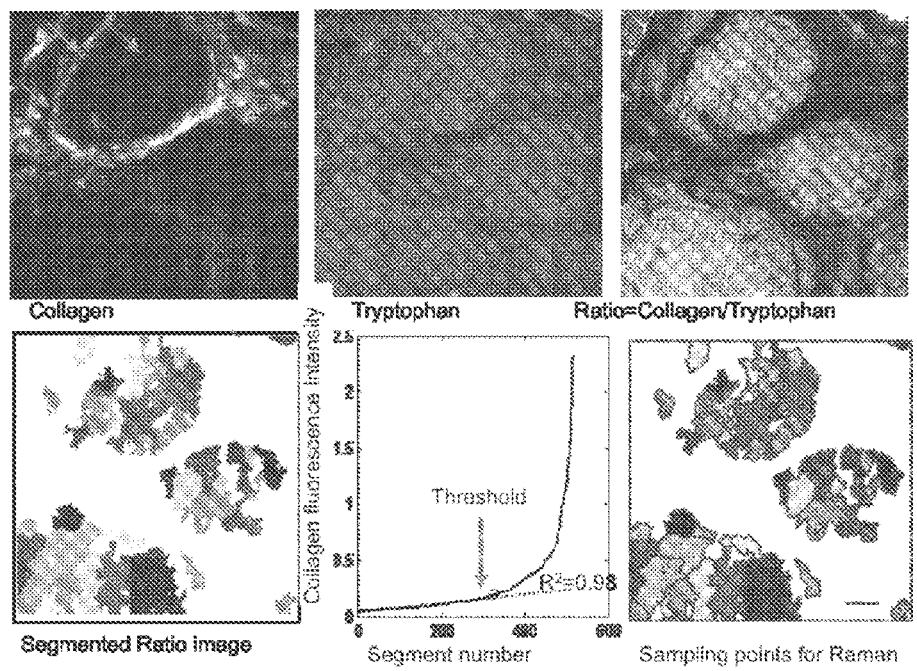
Figure 20:
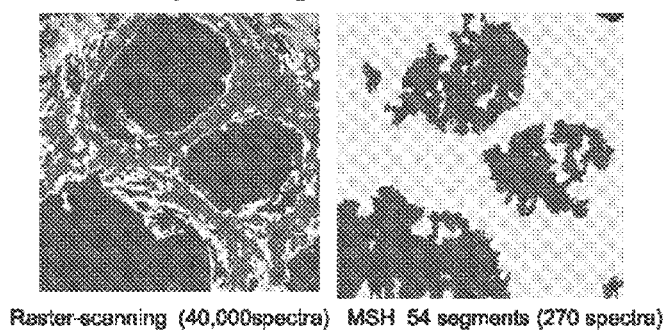
Figure 20:
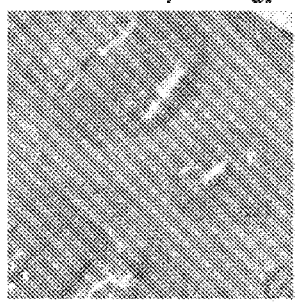
Figure 21:
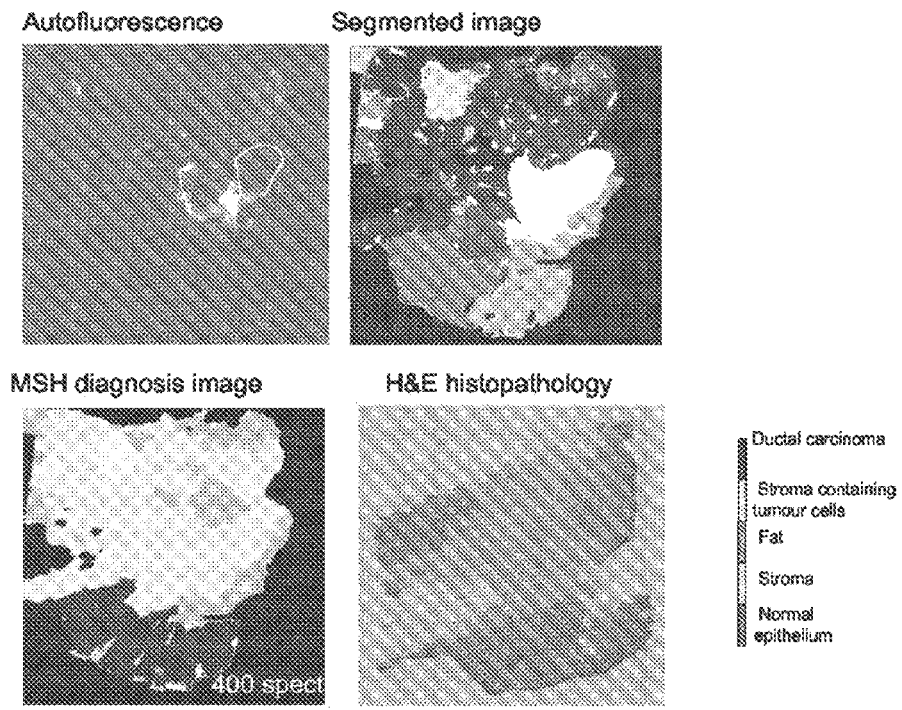
Figure 22:
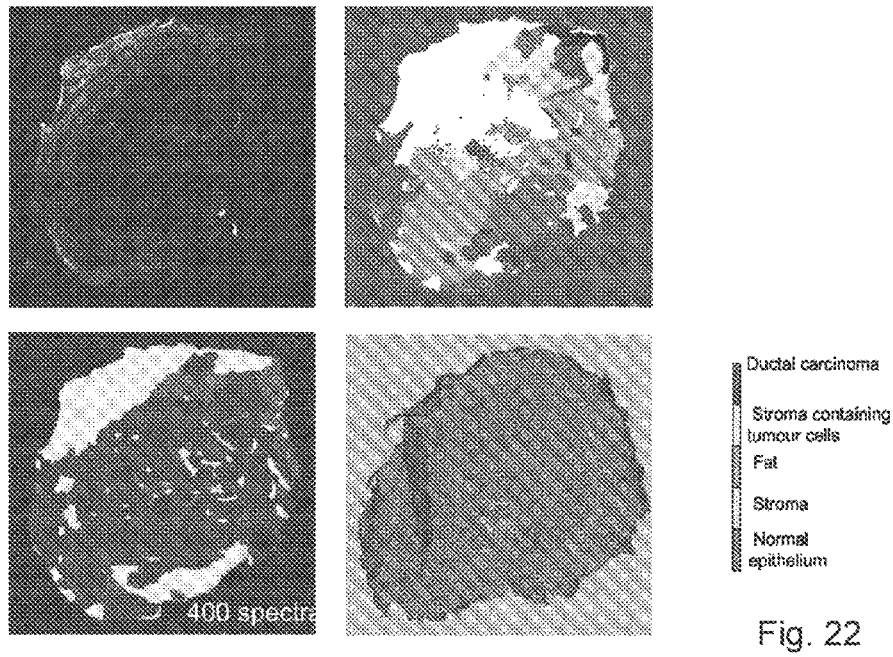
Figure 23:
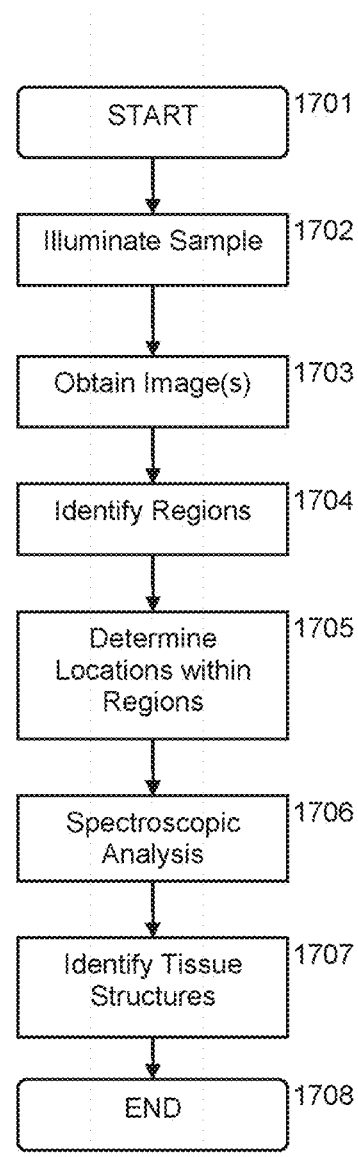

FIG. 19b is a plot of receiver operating characteristics of specificity as a function of sensitivity for the classification model (for DC-NST versus all other classes combined);

FIG. 20 illustrates a comparison between DC-NST diagnosis obtained by multi-modal spectral histopathology (MSH) and by raster scanning Raman spectroscopy;

FIG. 20a is a series of auto-fluorescence images for determining sampling points for Raman spectroscopy measurements in MSH to determine the presence of collagen (top left image), tryptophan (top middle image) and the ratio between collagen and tryptophan (top right image), with a derived segmented ratio image (bottom left) based on a threshold value (bottom middle image), within which sampling points for Raman spectroscopy are identified (bottom right image), where segments above the threshold in the collagen auto-fluorescence image are classified as stroma and excluded from the Raman spectra measurements;

FIG. 20b are Raman spectral diagnosis images derived from a 200×200 raster-scanning process covering 40,000 spectra (left image) and from a segmented and sampled image using 270 individual spectra (right image);

FIG. 20c is a conventional histopathology image of an adjacent tissue section of the sections imaged in FIGS. 20a-c, the tissue size being 2 mm×2 mm;

FIG. 21 MSH diagnosis for tissue sections from patients with DC-NST. a-c) DC-positive samples, d,e) DC-negative samples (red arrows indicate the false positive segments). The number of spectra measured for every sample is included. Histopathology images for adjacent sections are included for comparison. Tissue sizes: 6 mm×6 mm;

FIGS. 21 and 22 are a series of images illustrating the steps of an MSH diagnosis for tissue sections from patients with DC-NST, in which an autofluorescence image (top left) is used to generate a segmented image (top right) within which locations are identified for Raman spectroscopy, a series of spectra (400 in each case) are taken to identify each region as a particular tissue type (bottom left) and a comparison is given with conventional histopathology (bottom right), FIG. 21 indicating DC-positive samples and FIG. 22 DC-negative samples, the tissue size in each case being 6 mm×6 mm; and FIG. 23 is a schematic flow diagram illustrating a method according to an embodiment of the invention.

A new technique, termed herein Multimodal Spectral Histopathology (MSH), has been developed for accurate and objective diagnosis of large tissue layers excised during tissue conserving surgery. This technique may also have wider applications, for example in imaging and identifying tissue structures in vivo, as thin prepared sections do not necessarily need to be obtained for the technique to work. Since the technique does not require any tissue preparation steps (such as sectioning or staining), currently the diagnosis can be obtained in 10-30 minutes, making the technique suitable for intra-operative use. The current diagnosis time is, however, not a limitation of the technique but rather of the instrumentation and methods available. Ongoing developments indicate that diagnosis times of 1-5 minutes or less could be achieved in the near future, for example by using dedicated processing hardware or more powerful general computer processing.

A key feature of MSH is to abandon the slow raster scanning used in conventional Raman spectral imaging and instead use information regarding spatial correlation of a sample to select and prioritise the sampling points for Raman measurements. However, the spatial correlation of the sample is not available a priori. A method has been recently proposed for "selective sampling" in which the spatial correlation of the sample was calculated during the Raman measurements (J Biophotonics 2012, 3:220). While the selective scanning achieved speed up factors of up to 50× for model polymer samples, the performance on tumour diagnosis was not sufficient to allow accurate diagnosis of large tissue specimens.

To overcome these limitations, the new techniques described herein use an alternative optical technique to measure the spatial correlation of a sample prior to spectroscopy measurements. A key advantage of this alternative imaging modality is speed, enabling measurements to be taken in as little as a few minutes or less while retaining accurate delineation of tumours. It is important to note that this optical technique does not require a high specificity for tumour diagnosis. A spatial correlation map of a sample, obtained from a light image, is used to establish a sampling pattern for spectroscopy, which for typical samples (1-2 cm in extent) requires 800-1500 points. This is a vast reduction compared to the typical number of points (40,000 or more) that would be required to raster scan a similar size area at a sufficient resolution to ensure accurate identification of tissue structures while ensuring that no areas are overlooked.

In preferred embodiments, tissue auto-fluorescence intensity images obtained under UV illumination (using an acquisition time of typically around 1 minute or shorter) can be analysed by unsupervised (ie automated) image segmentation techniques to reliably divide the tissue into typically 100-200 segments (the number of which will depend on the variety of tissue structures evident in the sample) and delineate any tumour regions. By measuring only a small number of spectra, which may be a single spectrum but will typically be 3 to 10 spectra for each segment, around 1000 or fewer spectra per tissue sample may be required to provide a measurement in a few minutes that can be as accurate as a full raster scan taking many hours. The number of spectra may depend on the size of the segment. Large segments containing high amounts of collagen, which correspond to bright regions in the auto-fluorescence image, may be eliminated from spectroscopic analysis, since these can be confidently identified as not being of interest, for example when analysing for BCC. Measurement of the spatial correlation of the sample does not need to be limited to auto-fluorescence intensity or lifetime but could be obtained by other light imaging modalities even if these modalities may have lower chemical specificity.

Figure 1:
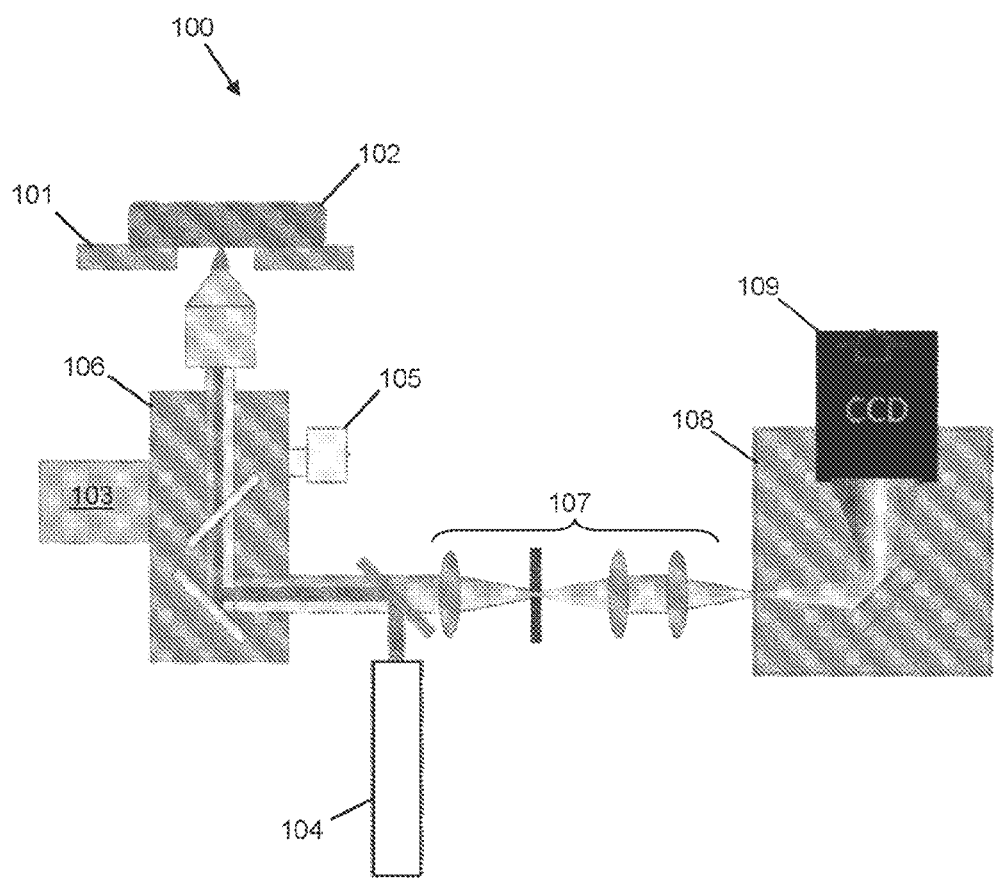
FIG. 1 is a schematic diagram of an apparatus according to an embodiment of the invention.

FIG. 1 illustrates schematically the key components of an apparatus 100 for performing measurements according to an embodiment of the invention. The apparatus 100 comprises a sample stage 101 for receiving a sample 102 to be analysed. The sample stage 101 may for example be a conventional computer-controllable motorised x-y-z microscope stage. An area of the sample is selectively illuminated by a first light source 103 and a second light source 104. In preferred embodiments the first light source 103 is a fluorescence excitation source, for example an ultraviolet light source configured to emit light at one or more wavelengths of interest depending on the sample to be analysed. The second light source 104 is preferably a laser, for example an infrared laser. A series of optics 106 is arranged to allow light from the first light source 103 to be directed towards the sample 102, and light emitted from the sample to be selectively directed towards a camera 105 and to a spectral analyser such as a spectrograph 108, or another device capable of spectral analysis, for example an arrangement of selected filters, and light sensor 109 (for example a CCD) via a further series of optics 107. A computer (not shown) is connected to the various components of the apparatus 100 to control the light sources 103, 104, the optics 106 and the sample stage 101, and to receive data from the camera 105 and spectrograph CCD 109 for further analysis. The computer may also be configured to carry out processing of the data received, such as identifying regions of interest in the illuminated sample area and identifying tissue structures from spectroscopic analysis of locations within the regions of interest. The processing may alternatively be carried out external to the apparatus, for example by a separate computer system.

In the methods described herein, all skin tissue samples were obtained during routine MMS at the Nottingham University Hospitals National Health Service (NHS) Trust.

Ethical approval was granted by the Nottingham Research Ethics Committee (07/H0408/172) and consent was obtained from all patients. The samples were kept frozen at −20° C. until used for Raman spectral measurements. 'Tissue block' herein refers to tissue layers thicker than 0.5 mm removed during MMS. 'Tissue sections' herein represent skin sections of 20 μm thickness cut from tissue blocks with a microtome (CM 1900 UV, Leica). After the Raman spectroscopy measurements, the analysed skin sections were stained by haematoxylin and eosin (H&E) and the diagnosis was provided by a consultant histopathologist. For tissue blocks, the diagnosis was based on adjacent H&E stained tissue sections.

Raman spectra were recorded using a custom built Raman micro-spectrometer based on an inverted optical microscope (Eclipse-Ti, Nikon) with a 50×/0.55 objective (Leica), 785 nm wavelength laser (Starbright XM, Torsana), spectrometer (77200, Oriel), back-illuminated deep-depletion CCD (DU401-A-BR-DD, Andor Technology) and automated sample stage (H107 Proscan II, Prior Scientific). Acquisition time for the Raman measurements was 2 seconds per position and the laser power at the sample surfaces was 200 mW. The spectrometer was calibrated using naphthalene and 1,4-bis(2-methylstyryl) benzene samples (both from Sigma-Aldrich, UK) to an accuracy of 0.5 $cm^{-1}$. Auto-fluorescence images of tissue sections were measured using wide-field fluorescence imaging system integrated to the Raman microscope; the system consisted of a mercury lamp (Nikon), CCD camera (01-QIClick-F-M-12 Mono, QImaging) and fluorescence filters for collagen (Semrock, DAPI-5060C-NTE-ZERO) and tryptophan (Semrock FF310-Di01-25×36, FF01-292/27-25, FF01-357/44-25). For tissue blocks, the auto-fluorescence images were recorded using a separate confocal-fluorescence microscope equipped with a 457.9 nm laser (C1, Nikon).

Raman spectral maps were recorded from skin tissue sections deposited on $MgF_2$ discs by raster scanning over areas of 1×1 $mm^2$ in 10 μm steps. The following pre-processing procedures were applied to all Raman spectra: removal of cosmic-ray peaks, subtraction of the background Raman signal of the microscope objective and $MgF_2$ substrate, subtraction of a baseline based on a rubber band method (the rubber bands were chosen between the regions 750-850 $cm^{-1}$, 855-950 $cm^{-1}$, 951-1050 $cm^{-1}$, 1135-1254 $cm^{-1}$, 1488-1600 $cm^{-1}$, 1675-1750 $cm^{-1}$), and normalisation to zero mean and unit variance [see references 22, 23]. For each spectral map a 3×3 moving average filter was applied and followed by two-step k-means clustering, with k=6×10. After the Raman spectral measurements, each tissue section was stained by H&E and the tissue structures (BCC, epidermis, hair follicle, dermis, inflamed dermis, muscle, sebaceous glands and fat) were identified by a consultant histopathologist. The pseudo-colour spectral images obtained by k-means clustering were correlated with the tissue structures revealed by the H&E images. The centroid spectrum of every cluster containing at least 10 measurement sites was included in the database and labelled as BCC, epidermis (including hair follicle), dermis, inflamed dermis, muscle and fat (including sebaceous glands). A maximum of 5 centroid spectra per class per patient were included in the database.

The spectral classification models for BCC were based on a data reduction method followed by a multivariate classification technique. Several data reduction methods (10 principal components from principal component analysis (PCA), 10 principal components followed by the multi-class linear discriminant analysis (LDA) based rank reduction [see for example references 24, 29, 30], ratios of band areas) and classification techniques (LDA, quadratic discriminant analysis, multinomial logistic regression (MNLR) were compared based on a 5-fold cross-validation algorithm. All classifiers were tuned to the regime providing 95% sensitivity on the training data. The models were tested using an independent set of tissue samples from new patients. The model with the best classification performance for BCC diagnosis was then selected and used for imaging and multimodal spectral histopathology.

For tissue sections, sample preparation was the same as for the samples used for the classification model. For tissue blocks, samples were deposited on $MgF_2$ coverslips (0.17 mm thick) and were maintained in phosphate buffer saline (PBS) during the measurements. The Raman spectra from a selected region of the tissue were acquired at 10 or 20 μm steps with 2 seconds integration time at each position. After RMS measurements, all spectra were pre-processed, as discussed above. The same two-step k-means clustering algorithm was used to identify the tissue regions with similar Raman spectra. The objective diagnosis of each tissue region in the pseudo-colour spectral image was obtained by applying the classification model to the centroid spectrum of each cluster [see references 8, 25, 26].

Figure 2:
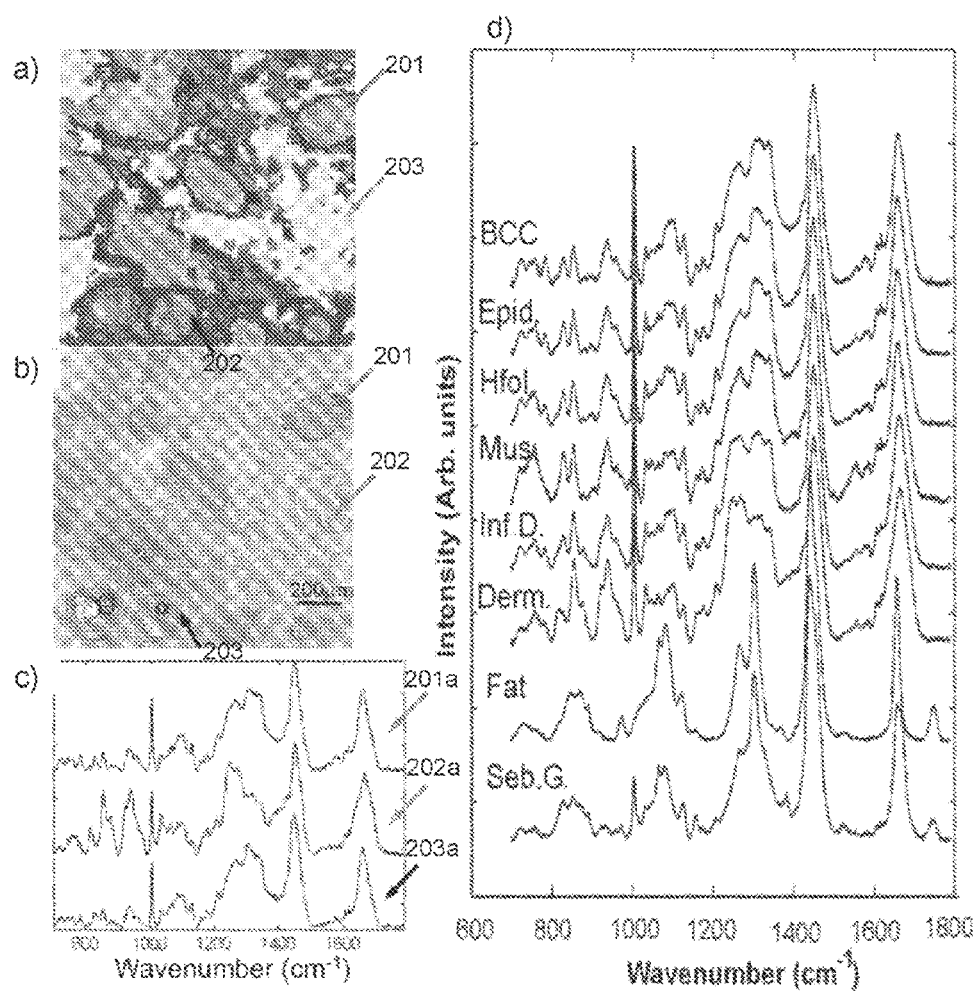
FIGS. 2a and 2b are images of a tissue sample derived from Raman spectra assignment (FIG. 2a) and conventional HE staining (FIG. 2b)
FIG. 2c is a plot of mean spectra for three different tissue structures in the sample of FIGS. 2a and 2b.
FIG. 2d is a series of plots for mean Raman spectra for various tissue structures.

A first step in the development of a spectral classification model is to establish a method to assign the measured Raman spectra to the correct tissue structures in the skin samples. An unsupervised two-step k-means clustering was applied on the datasets of Raman spectra acquired by raster scanning from tissue regions of 1 mm×1 mm, in order to produce pseudo-colour images based on spectral similarities. FIG. 2a shows a typical example of a skin tissue containing nodular BCC 201, hair follicles 202 and regions of healthy and inflamed dermis 203. By comparing this pseudo-colour image with the histopathology image obtained by H&E staining of the tissue after completion of the Raman spectral measurement, the centroid spectra 201a, 202a, 203a for each cluster were attached a label corresponding to BCC or healthy skin structures, such as epidermis, hair follicles, inflamed dermis, dermis, fat, sebaceous gland and muscle. For this task, a total number of 550,000 Raman spectra were recorded from 55 patients with high-risk BCC on the face (nose, ear, eyelid, eyebrow and temple). After k-means clustering, 492 centroid Raman spectra were included in the training dataset of the classification model (6 classes): 92 for BCC, 75 for epidermis (combined with hair follicles), 67 for inflamed dermis, 148 for dermis, 75 for fat (combined with sebaceous glands), and 35 for muscle. FIG. 2d presents the mean of the Raman spectra corresponding to BCC and other tissue structures included in the model (epidermis, hair follicles, inflamed dermis, dermis, fat, sebaceous gland and muscle). In agreement with the previous reports, the Raman spectra of BCC indicates more intense bands corresponding to DNA compared to other tissue structures (e.g. O—P—O symmetric stretching 788 $cm^{-1}$, $PO^{2-}$ 1098 $cm^{-1}$ and guanine 1577 $cm^{-1}$) while the Raman spectra of dermis were dominated by bands specific to collagen fibres (e.g. 851 and 950 $cm^{-1}$ bands assigned to proline and hydroxyproline) [reference 19]. The higher number of cells in the inflamed dermis regions led to a higher contribution from DNA bands in the Raman spectra. The Raman spectra of skin structures rich in lipids, such as sebaceous glands and fat regions, show specific bands characteristic to C—H, C—C and C=C vibrations (850 $cm^{-1}$, 1070 $cm^{-1}$, 1267 $cm^{-1}$, 1301 $cm^{-1}$, 1450 $cm^{-1}$, ~1660 $cm^{-1}$) [references 19, 20]. The classification models were optimised for BCC diagnosis at 95% target sensitivity. The best performance for BCC (i.e. the highest sensitivity for BCC versus non-BCC) was obtained when the data reduction was based on principal component analysis (10 components retained to reduce noise) followed by rank-reduced multi-class linear discriminant analysis to define K−1 canonical features, where K=6 was the number of classes. These 5 spectral features were then used with the multinomial logistic regression classifier. The confusion matrix for the 5-fold cross-validation is shown below, showing 95.3±5.8% sensitivity and 94.6±3.1% specificity for BCC classification (errors represent the 95% confidence intervals).

Confusion matrices

| True | Unk. | BCC | Epid. | Infl. | Derm | Fat | Musc. |
|---|---|---|---|---|---|---|---|
| 5-fold Cross-validation | | | | | | | |
| Unk. | 0 | 0 | 0 | 0 | 0 | 0 | 0 |
| BCC | 0 | 95.3 | 3.3 | 1.4 | 0 | 0 | 0 |
| Epid. | 0 | 13.1 | 81.0 | 4.4 | 0 | 0 | 1.5 |
| infl. | 0 | 13.9 | 1.2 | 57.1 | 27.7 | 0 | 0 |
| Derm | 0 | 0 | 1.1 | 14.1 | 84. | 0 | 0 |
| Fat | 0 | 0 | 0 | 0 | 0 | 100 | 0 |
| Musc. | 0 | 0 | 3.9 | 0 | 1.9 | 0 | 94.3 |
| Independent validation | | | | | | | |
| Unk. | 0 | 0 | 0 | 0 | 0 | 0 | 0 |
| BCC | 0 | 100 | 0 | 0 | 0 | 0 | 0 |
| Epid. | 0 | 16.7 | 80.0 | 3.3 | 0 | 0 | 0 |
| Infl. | 0 | 16.7 | 0 | 33.3 | 50 | 0 | 0 |
| Derm | 0 | 2.0 | 0 | 9.8 | 88.2 | 0 | 0 |
| Fat | 0 | 0 | 0 | 0 | 0 | 100 | 0 |
| Musc. | 0 | 0 | 18.2 | 0 | 0 | 0 | 81.8 |

The classification model was then tested on an independent set of skin samples from 22 patients with high-risk BCC on the face (220,000 individual Raman spectra), for which the Raman spectra were measured and pre-processed in the same way as the spectra included in the training dataset (total 199 centroid spectra). The independent dataset consisted of 58 centroid Raman spectra corresponding to BCC and 141 centroid spectra corresponding to the other classes. The confusion matrix above shows that BCC was classified with 100% sensitivity and 92.9% specificity, which is in good agreement with the cross-validation results.

Figure 3:
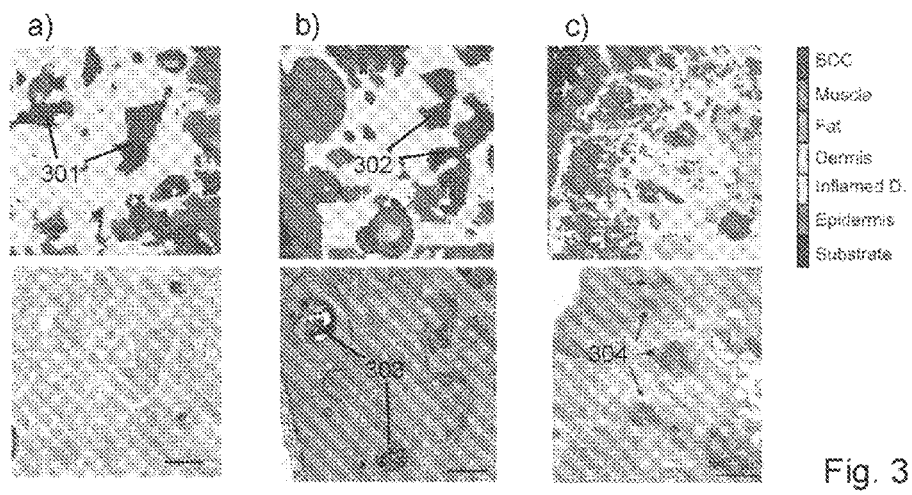
FIGS. 3a to 3c are raster scanned Raman spectrometry images and corresponding HE stained histopathology images of tissue sections (scale bar=200 µm)
Figure 4:
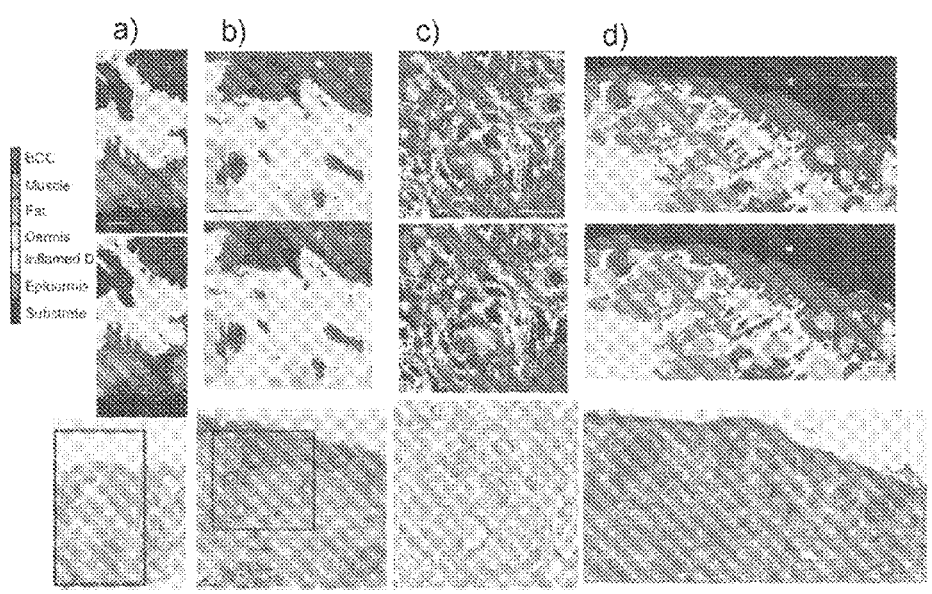
FIGS. 4a to 4d are raster scanned Raman spectrometry images and corresponding HE stained histopathology images of unsectioned tissue blocks (scale bar=200 µm)

FIG. 3 shows typical quantitative diagnosis images (upper images) obtained by applying the Raman classification model on Raman spectral maps obtained by raster scanning on independent skin samples (1 mm×1 mm regions were selected to allow an acquisition time for the Raman measurements of ~3-5 hours at 100×100 pixels resolution), together with corresponding HE stained histopathology images (lower images). FIG. 3a represents a skin section containing nodular BCC 301, hair follicles and dermis. All BCC regions 301 were correctly diagnosed by the classification model (including tumours as small as 40×40 μm 2), although small regions of inflamed dermis containing large number of lymphocytes and few basal layer regions around hair follicles were also classified as BCC. The majority of the lymphocytic inflamed dermis was diagnosed as healthy tissue (classified as inflamed dermis or epidermis). However, as indicated by the results in the confusion matrix, misclassification between healthy tissue structures (mainly dermis, inflamed dermis and epidermis) was observed, because the classification model was optimised to discriminate between BCC and healthy tissue rather than among healthy tissue structures. The results are also confirmed in FIG. 3b showing another example of skin sample containing nodular BCC 302, in which only small regions of basal layers at the edges of the hair follicles 303 were misclassified as BCC. FIG. 3c presents an example of a skin section for which the traditional H&E histopathology diagnosis of the skin structures 304 that are morphologically similar to BCC can be difficult. After tissue sectioning and histopathology evaluation of sequential layers, the tissue sample was diagnosed as negative (ie BCC-free) and the structures were identified as hair follicles. FIG. 3c shows that the Raman spectral classification model provided the correct diagnosis for all hair follicles, based only on the molecular information in the examined tissue section, and without requiring the evaluation of adjacent sections. Although the classification model was built using Raman spectra measured from tissue sections, objective diagnosis can also be obtained by analysing the surface of tissue blocks removed during MMS (without sectioning) from patients with high-risk BCC on the face, as shown in FIG. 4. The comparison between the spectral images (upper and middle images) and the histopathology images (lower images) of adjacent sections show that high diagnosis accuracy can also be obtained for skin blocks containing nodular BCC when using 95% target sensitivity. However, in the case of tissue blocks containing superficial and infiltrative BCC, indicated in FIGS. 4b and 4c, most of the small tumours (50-100 μm) were not correctly diagnosed. These diagnosis errors were attributed to the deeper sampling volume when measuring Raman spectra of tissue blocks compared to the tissue sections used for building the model. Such errors are likely to affect more the diagnosis of smaller BCC tumours, such as infiltrative and superficial BCC rather than nodular BCC. However, when the target sensitivity of the Raman spectral classification model was increased to 100% in order to account for the differences is sampling volume, the diagnosis images improved and all BCC tumours were correctly diagnosed in agreement with the histopathology images, as shown in the middle images of FIGS. 4b and 4c. FIG. 4d presents a typical example of BCC-free tissue block, showing that the spectral classification model maintained a high diagnosis specificity for BCC even at 100% target sensitivity.

For measurements of tissue sections according to the new technique, the ratio of the auto-fluorescence intensity images corresponding to tryptophan (excitation 292 nm/emission 357 nm) and collagen (excitation 377 nm/emission 447 nm) were segmented using an unsupervised segmentation algorithm [see reference 27] and Matlab code developed by Naidu [reference 28]. Five Raman spectra were recorded per segment, the sampling points being determined by a space-filling algorithm (the edge pixels of the segments were trimmed off in order to avoid measurement at the boundaries). Sample positioning was automated using a programmable microscope stage. To avoid the out-of-focus problem in Raman spectral measurements for tissues larger than 3 mm×3 mm, the tissues were divided into a 3×3 grid, and focusing was manually adjusted at each region. The segments smaller than 0.01 mm$^2$, normally found within the dermis, were ignored and were labelled as dermis. The non-linear trend of the averaged collagen auto-fluorescence intensity in each segment was used to identify the large tissue areas corresponding to dermis that elicited strong collagen auto-fluorescence. These tissue regions were classified as dermis based and no Raman spectra were measured from these segments.

The following pre-processing was applied to the Raman spectra: removal of spectra contaminated by the dyes used in MMS (the segments with more than three contaminated spectra were labelled as unknown), de-noising based on an independent set of Raman spectra from ten patients (50,000 spectra) using a singular value decomposition algorithm with 50 loadings, followed by the procedures described above (removal of cosmic-ray peaks, subtraction of the background and baseline, normalisation to zero mean and unit variance). Each Raman spectrum was then labelled using a classification model. A segment was diagnosed as BCC when at least two Raman spectra in the segment were classified as BCC. For the other classes, the diagnosis was established by a majority vote rule.

A first step in an exemplary embodiment of a method according to the invention involves taking measurements of the spatial correlation of the sample. A sample, which may be one excised from a patient, is placed on the microscope stage to which a method of optical measurement has been attached. The aim of this additional optical measurement is not to provide diagnosis but rather to establish the regions of the sample that are likely to be chemically broadly similar. Such regions can be grouped in a number of segments, for example around 100-200 segments. In the case of skin and breast tissue sections, integrated wide-field auto-fluorescence for collagen and tryptophan (using UV excitation) has been used to obtain images in around 1 minute. In the case of thick tissue layers, spatial correlation of samples has been measured by confocal fluorescence microscopy. Dynamic speckle illumination or fluorescence life-time imaging are other alternative imaging modalities. If more than one optical technique is used for measuring the spatial correlation map, the different optical images can be combined into a multivariate image which is then divided into a plurality of segments using a suitable unsupervised (ie automatic) image segmentation algorithm. Additional information from the optical image can be used to exclude parts of the image from spectroscopic analysis or to establish the probability of a certain segment to be tumour. Examples include large dermis regions, which will tend to be bright in the collagen emission and therefore a very low probability of having BCC. Dark regions in a tryptophan image may indicate a lack of proteins, which are also therefore are unlikely to be BCC. These regions can be eliminated from being considered during further spectroscopic analysis.

In a second step the locations for sampling points for spectroscopic measurements are generated. This can be done automatically, ensuring that all relevant segments in the spatial correlation map are sampled. This can carried out be a simple method such as by determining a set number of randomly placed points per segment, or by a more advanced method that takes into account the properties of the segment. In relation to size, for example, smaller regions may require fewer points for analysis, while larger regions may require more points. Darker regions in tryptophan images are likely to be fat, thereby requiring fewer points. A chemically homogenous segment would also require fewer points. Raman spectra are then measured at the identified locations, either by moving the sample with the automated microscope stage or by scanning a laser beam across the sample. The spatial correlation map may also be used to prioritise the sampling points, such that once each region has been confidently identified no further spectroscopic measurements need to be taken, thereby saving further time.

In a third step, each segment identified in the sample is classified according to the spectroscopic analysis. There are various ways of establishing a diagnosis for a sample, for example based on a pre-existing Raman spectral classification model, measured Raman spectra of the sample and the spatial correlation map. A simple method can be based on the calculation of the mean representative spectrum for each segment. A variance spectrum can also be calculated to establish a confidence level on diagnosis and to apply a pre-existing classification method on the Raman spectrum corresponding to each segment to provide the diagnosis for the segment. The methods for obtaining the classification models are available in the literature, for example as disclosed in WO 2010/131045, the contents of which are incorporated herein by reference. In another method, the classification model can be applied on each Raman spectrum and a majority vote could be applied to obtain the diagnosis for each segments. This method would allow adjustment of the sensitivity of the diagnosis technique.

FIGS. 5a-f and 6a-c illustrate the steps involved in performing analysis on a sample according to an embodiment of the invention, as compared with conventional analysis using raster-scanned spectroscopy and by HE stained histology. Autofluorescence images were obtained via wide-field imaging, using excitation and emission wavelengths corresponding to collagen (FIG. 5a) and tryptophan (FIG. 5b). Images for tryptophan (excitation 292 nm/emission 357 nm) and collagen (excitation 377 nm/emission 447 nm) were recorded, using around a 2 minute acquisition time per image. The ratio of these images to highlight the tissue structures, as shown in FIG. 5c, was then used to obtain a segmented image, as shown in FIG. 5d. In each of FIGS. 5a-d, regions known in retrospect to be BCC tumours 501 and sebaceous glands 502 are indicated by arrows. Autofluorescence imaging has high sensitivity for detection of BCC as tumours can be well delineated in both collagen (dark regions) and tryptophan (grey regions) images. However, these results confirm the low specificity of auto-fluorescence imaging as BCC cannot be discriminated reliably from other tissue structures, such as sebaceous glands, hair follicles or epidermis.

An unsupervised image segmentation algorithm was used to divide the ratio image into segments and determine the contour of the skin sample. Since dermis elicits a stronger auto-fluorescence emission compared to other tissue structures when excited with 377 nm light, an automated method was established to provide a classification for dermis directly from the collagen auto-fluorescence images. First, the average intensities of collagen fluorescence within each segment were calculated and fitted with a linear function from low to high intensities. A threshold intensity was determined when the linear fit had $R^2$ less than 0.98 for tissues sections (0.995 for tissue blocks) and all segments with average collagen auto-fluorescence intensity above this threshold were classified as dermis. Other ways of determining a threshold value may alternatively be used, such as a preset proportion of the range of fluorescence intensity values in the image. In addition, segments smaller than a predetermined minimum size, for example 0.01 mm$^2$ (corresponding to a region 100 µm square) or smaller may be excluded, as these could be considered too small to be multi-cellular regions that may be BCC. The minimum size may alternatively be defined according to linear extent, such that any segments having a maximum linear extent less than 100 µm or smaller may be discounted.

For all other segments, a space-filling algorithm was used to generate five points for each region that determined the sampling locations for subsequent Raman spectral measurements. FIG. 5f shows that after segmentation and classification of dermis segments based on the collagen autofluorescence intensity, only around 70 regions were retained for Raman spectral measurements (in this case corresponding to 350 sampling points, i.e. 5 points per region).

FIG. 6a is an image generated from a raster scan of the sample area of FIGS. 5a-f, where a 200×200 array of scan points, defining a series of 40,000 spectra, were taken and matched to various known tissue types, indicated as BCC, muscle, fat, dermis, inflamed dermis, epidermis and substrate. FIG. 6b is a corresponding image generated from a method according to the above described embodiment of the invention, using 350 spectra as indicated by the segmented image in FIG. 5f. In this embodiment, a segment was diagnosed as BCC when at least two Raman spectra per segment were classified as BCC. For all other classes, the tissue structure was established by a majority vote rule, i.e. at least 50% of spectra corresponding to the same structure. FIG. 6c is a conventional H&E stained histopathology image of an adjacent tissue section, in which arrows indicate BCC tumours 601 and sebaceous glands 602. From a comparison between the different FIGS. 6a-c, it is clear that the method according to this embodiment is as good as, if not better, than existing raster scan spectroscopy and conventional histopathology methods, at least for determining the presence and extent of BCC regions.

FIGS. 6a-c show that the diagnosis images obtained by raster scanning Raman spectroscopy and MSH were in excellent agreement with conventional H&E histopathology. However, MSH provided a dramatic decrease in the acquisition time as it requires over 100 times fewer Raman spectra compared to raster scanning.

A further example of a method according to the invention is illustrated in FIGS. 7a-d, 8 and 9a, 9b, in which auto-fluorescence images for collagen and tryptophan (FIGS. 7a, 7b) were used to determine the spatial correlation of the skin tissue sample. Arrows 701 in FIGS. 7a-c show that the basal cell carcinoma (BCC) regions are well delineated, but that auto-fluorescence imaging has low specificity for BCC, as a BCC area can be easily confused with sebaceous gland, fat or hair follicles, as indicated by arrows 702. The ratio between the auto-fluorescence images is used to produce a segmented image (FIG. 7c), highlighting the spatial correlation of the sample, which is then populated with locations for spectroscopic sampling (shown in FIG. 8). A comparison between diagnosis images obtained by raster scanning using 40,000 Raman measurements (FIG. 9a) of a selected region of the tissue and the diagnosis of the same area using MSH with only 773 Raman measurements (equivalent to ~12 minutes), (FIG. 9b) indicates excellent agreement between MSH diagnosis, raster-scanning and histopathology image (FIG. 7d) of an adjacent section.

FIGS. 10 to 13 illustrate further typical examples of quantitative diagnosis by MSH for 20 µm thick sections cut from tissue blocks excised during MMS, using varying numbers of spectra samples. FIG. 10 indicates a de-bulk sample with large nodular BCC (974 spectra), FIGS. 11 and 12 samples containing 100-1000 µm BCC tumours (823 and 779 spectra respectively), and in FIG. 13 a BCC-free sample (807 spectra). The BCC tumours in FIGS. 11b and 12b are indicated by arrows 1101, 1201. The scale bars in each of FIGS. 10a, 11a, 12a and 13a are 1 mm. For de-bulk samples showed in FIG. 10, although the fraction of the sample that was classified as dermis based on the auto-fluorescence intensity threshold was small, the retained segments for Raman measurements were generally large and the diagnosis was obtained with a total of only 974 Raman spectra. FIGS. 11 and 12 present typical tissue sample in which the BCC represents around 5-10% of the total tissue area. These samples have a high number of small tissue structures (fat, hair follicles and BCC) that are well separated into individual segments by the segmentation algorithm. MSH remains efficient because the large areas of dermis can be classified using the auto-fluorescence intensity and can be excluded from the Raman measurements. The results show that accurate diagnosis by MSH can be obtained with only 700-1000 Raman spectra, and that BCC tumours as small as around 100-150 µm in size can be reliably detected. The MSH method was also able to provide the correct diagnosis of BCC-free samples, as shown in FIG. 13.

MSH may also be used to provide quantitative diagnosis for un-sectioned tissue blocks excised during MMS. If accurate and objective diagnosis of the tumour margins can be obtained by examining only the bottom surface of the excised tissue blocks without sectioning and preparation of frozen sections, these time-consuming procedures would no longer be required and the surgery time and costs could be further significantly reduced. However, for tissue blocks, the auto-fluorescence images obtained with a wide-field auto-fluorescence imaging system integrated to the Raman microscope were blurred because of the out-of-focus light, and were consequently not suitable for segmentation. Therefore, auto-fluorescence images of tissue blocks were measured on a separate confocal fluorescence microscope equipped with a 457.9 nm laser. The samples were subsequently moved to the Raman microscope for spectral measurements, ensuring preservation of location information. In preferred embodiments of the invention, both the light images and spectroscopy information would be carried out on a sample in the same instrument to ensure preservation of location and to minimise measurement times.

Examples of MSH diagnosis images for tissue blocks containing BCC are shown in FIGS. 14 and 15, incorporating corresponding histopathology images obtained from adjacent sections. These results show that confocal microscopy provided high contrast images that were efficiently segmented by the algorithm. The BCC tumours 1401, 1501 were well separated from the surrounding healthy tissue and were identified as individual segments. FIG. 14 shows that MSH provided the correct diagnosis for BCC requiring only 608 Raman spectra. The diagnosis was obtained using a classification model adjusted for 100% target sensitivity. For the other sample in FIG. 15, correct diagnosis of BCC was correct only for tumours larger than ~700 µm. Although the confocal images allowed very efficient segmentation of BCC regions as small as 150 µm, the misalignment between the confocal fluorescence microscope and the Raman microscope led to sampling errors, resulting in misdiagnosis. However, such errors can be eliminated with confocal auto-fluorescence imaging integrated into the Raman microscope, as in general the quality of image segmentation was higher for the confocal images compared to the wide-field images.

FIGS. 14 and 15 demonstrate that MSH can provide accurate and objective diagnosis of BCC in both tissue sections and thick tissue blocks with only 600-1000 Raman spectra. Considering an acquisition time of 4 minutes for the auto-fluorescence images (8 minutes for confocal fluorescence), 2 seconds integration time for each Raman spectrum, and 2 minutes for the image segmentation processing, the current diagnosis time for MSH was around 25-40 minutes. This diagnosis time compares favourably with the current practice of frozen section histopathology during MMS, which requires 20-120 minutes for sample preparation only. However, the computational steps required for image analysis could be optimised for MSH to be completed in less than 1 minute, for example by using a dedicated hardware module such as a field-programmable gate array. The speed of Raman spectral measurements could also be readily increased, for example by using a Raman microscope with a multifocus or line-shaped laser to measure 10 to 48 Raman spectra simultaneously. As the MSH diagnosis is no longer limited by the time-consuming tissue sectioning and staining preparation steps, such further developments have the potential to allow intra-operative diagnose of tissue layers and blocks within few minutes or even less, providing a fast and objective feedback to the surgeon on whether further tissue removal is required or not.

FIG. 16 illustrates a typical example of MSH diagnosis for BCC in skin tissue sections (20 micron thickness) compared to conventional histopathology (FIG. 16d) for adjacent sections. BCC regions in the histopathology image and the corresponding MSH image in FIG. 16a are indicated by arrows 1601.

A classification model for quantitative diagnosis of breast tumours based on Raman spectra using MSH has been developed, as illustrated in FIGS. 17 to 22. FIGS. 17 and 18 illustrate an example of using the two-step k-means clustering algorithm for assigning Raman spectra to breast tissue structures and ductal carcinoma required for training the classification model (scale bar: 300 µm). Typical centroid Raman spectra are shown for the clusters indicated by arrows for: ductal carcinoma 1801, stroma 1802 and stroma containing tumour cells 1803.

Figure 19:
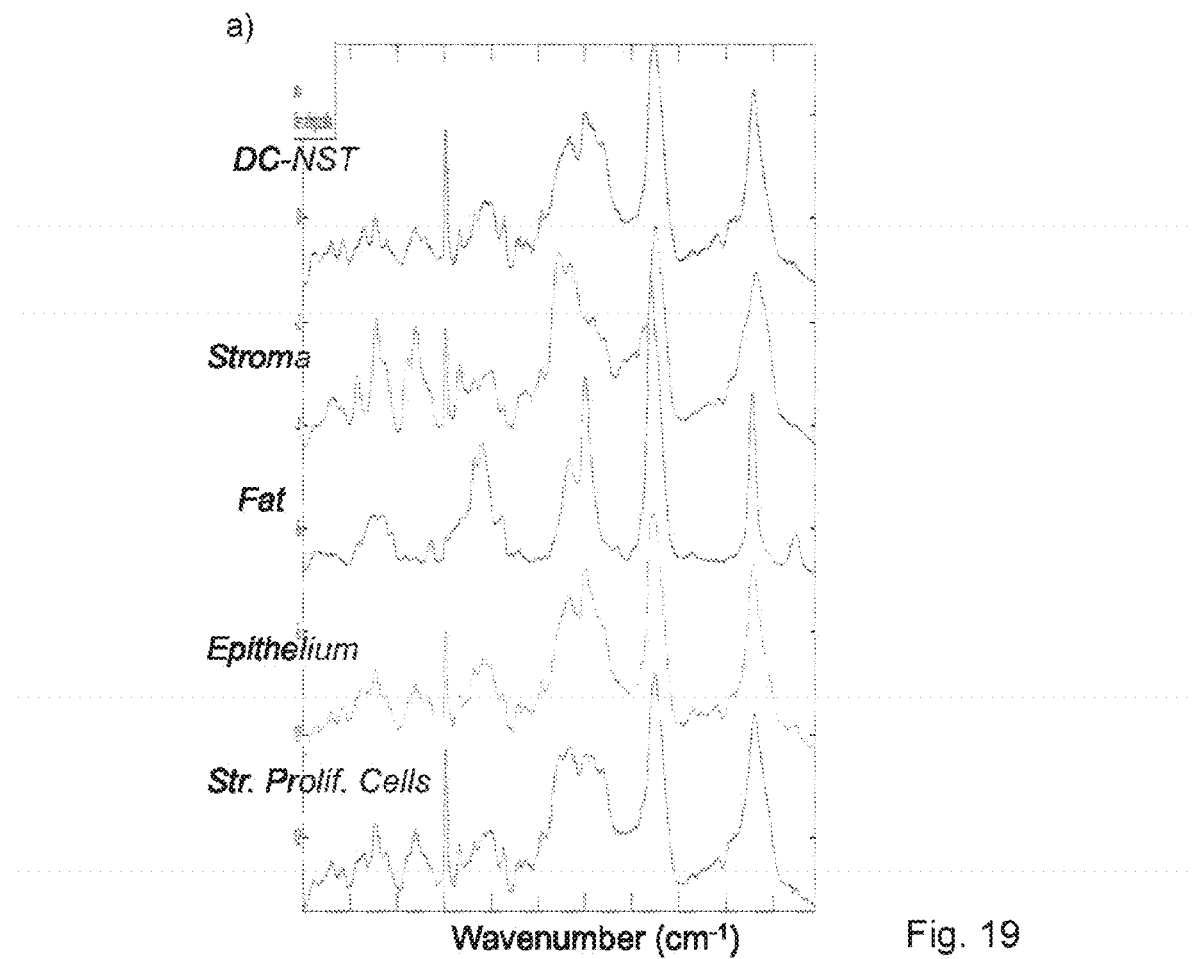
Figure 19:
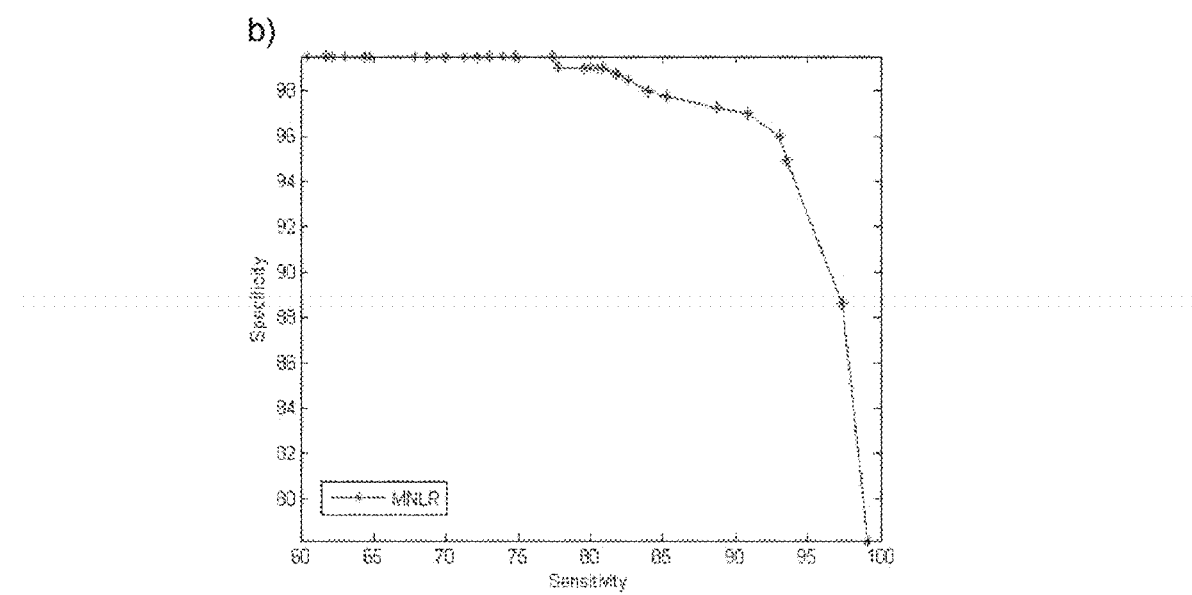

FIG. 19 illustrates the mean Raman spectra (FIG. 19a) of healthy breast tissue structures and tumours, indicating the spectra associated with ductal carcinoma (DC-NST), stroma, fat, epithelial cells, stroma containing proliferating tumour cells (Str. Prolif. Cells). The confusion matrix below for a 5-fold cross-validation of actual class versus predictive class, with a target 95% sensitivity, indicates a good match between predicted and actual classes in each case. The calculated sensitivity was 95% and specificity 96%. FIG. 19b indicates the receiver operating characteristic for the classification model, comparing DC-NST versus all other classes combined.

|  |  | Predictive Class | | | | |
| --- | --- | --- | --- | --- | --- | --- |
|  |  | DC NST | Str. | Fat | Epith. | Str. + t. cells |
| Actual Class | DC NST | 95.1 | 0 | 0 | 1.8 | 3.1 |
|  | Str. | 0 | 99.5 | 0 | 0 | 0.5 |
|  | Fat | 0 | 0 | 100 | 0 | 0 |
|  | Epith. | 3.4 | 0 | 3.4 | 91.7 | 1.4 |
|  | Str. + t. cells | 0 | 0 | 0 | 0.56 | 99.5 |

FIG. 20 illustrates a series of images indicating a comparison between DC-NST diagnosis obtained by MSH and raster scanning Raman spectroscopy. In FIG. 20a, autofluorescence images are given for collagen (top left), tryptophan (top middle) and the ratio between collagen and tryptophan (top right). The auto-fluorescence images are used to generate a segmented image (bottom left) and to determine sampling points for Raman spectroscopy measurements (bottom right). In this case, segments above the threshold (bottom middle image) in the collagen auto-fluorescence image are classified as stroma and are excluded from the Raman spectra measurements. FIG. 20b indicates diagnostic images obtained by 200×200 raster-scanning Raman spectroscopy, amounting to 40,000 spectra (left image) compared to MSH diagnosis using only 270 spectra based on locations within the segmented image (right image). For comparison, a conventional histopathology image of an adjacent tissue section (2 mm×2 mm) is indicated in FIG. 20c. As can be seen, the method according to the invention can be used to provide a very substantial increase in speed, in this case by a factor of 40,000/270=148 compared to conventional raster scanning, without significantly compromising on the accuracy of diagnosis.

FIGS. 21 and 22 illustrate MSH diagnosis for tissue sections from patients with DC-NST, in which FIG. 21 illustrates a DC-positive sample and FIG. 22 a DC-negative sample. In each figure, the autofluoresence image (top left), the segmented image (top right), and MSH diagnosis image (bottom left) and a comparative histopathology image (bottom right) are indicated. The number of spectra measured for each sample is 400. Histopathology images for adjacent sections are included for comparison. Tissue sizes: 6 mm×6 mm.

FIG. 23 is a schematic flow diagram illustrating in general terms a method according to the invention. The method begins (step 1701) with preparing a sample for analysis, which may involve obtaining a tissue section or block, or may optionally involve positioning apparatus for performing the invention adjacent a sample area to be analysed. The sample area is then illuminated (step 1702), and one or more images are taken of the sample area (step 1703), for example using UV autofluorescence. An image obtained is then analysed to determine regions for further analysis (step 1704), which may involve discounting selected regions on the basis of a threshold. Locations for spectroscopic analysis are then defined within the determined regions (step 1705). Spectroscopic analysis is then performed at the determined locations of the sample area (step 1706). From the spectra obtained, tissue structures are then identified for each of the regions (step 1707). The method then ends (step 1708), typically by producing an image of the sample area coloured according to the different tissue structures identified.

In summary, the invention described herein represents a new microscopic method that has been shown to be suitable for quantitative diagnosis of BCC in skin tissue samples excised during MMS or tumours in breast tissue, although the method may have wider applications. First, a classification model based on Raman spectra of skin tissue structures and BCC was developed which allowed objective diagnosis and imaging of BCC in tissue sections and blocks, based entirely on the molecular composition of the tissue structures. However, due to the time-consuming raster scanning, the diagnosis was limited to 1 mm×1 mm tissue regions, which is not satisfactory considering that the tissue samples excised during MMS are typically 10 mm×10 mm in size. To overcome this limitation, we have developed a new method that combines the speed of tissue auto-fluorescence imaging and chemical specificity of Raman spectroscopy: auto-fluorescence imaging was used to measure the spatial correlation of the sample, which was then used to prioritise and reduce the number of Raman spectra by a factor higher than 100 without loss of sensitivity. Using skin samples from new patients, MSH was able to provide the correct diagnosis within 25-40 minutes, which compares favourably with the current preparation time of frozen sections during MMS (20-120 minutes for tissue preparation only). The main advantage of MSH compared to the conventional histopathology is that objective diagnosis can be obtained without any additional sample preparation, therefore the surgery time and costs can be significantly reduced. Further technological developments and optimisation of the image processing algorithms could further reduce the diagnosis time to few minutes or less, such that several tissue removals and diagnosis could be performed within a single local anaesthetic dose. While this study focused on BCC and breast tumours, MSH can be extended to other cancers. MSH may be used to provide intra-operative diagnosis and ensure clear margins during tissue conserving surgery for other tissues, such as breast or lung, where currently histopathological diagnosis of tissues is not performed intra-operatively because of the time-consuming procedures for sample preparation and evaluation (e.g. breast conserving surgery).

Other embodiments are intentionally within the scope of the invention as defined by the appended claims.

REFERENCES

1. Frederic, Mohs, A Microscopically Controlled Method of Cancer Excision. Arch Surg, 1941. 42(2): p. 279-295.
2. Mosterd, K., et al., Surgical excision versus Mohs' micrographic surgery for primary and recurrent basal cell carcinoma of the face: a prospective randomised controlled trial with 5 years' follow up. Lancet Oncology, 2008. 9(12): p. 1149-1156.
3. Mogensen, M. and G. B. E. Jemec, Diagnosis of nonmelanoma skin cancer/keratinocyte carcinoma: A review of diagnostic accuracy of nonmelanoma skin cancer diagnostic tests and technologies. Dermatologic Surgery, 2007. 33(10): p. 1158-1174.
4. Raab, S. S. and D. M. Grzybicki, Quality in Cancer Diagnosis. CaDa Cancer Journal for Clinicians, 2010. 60(3): p. 139-165.
5. Nijssen, A., et al., Discriminating basal cell carcinoma from its surrounding tissue by Raman spectroscopy. Journal of Investigative Dermatology, 2002. 119(1): p. 64-69.
6. Lieber, C. A., et al., In vivo nonmelanoma skin cancer diagnosis using Raman microspectroscopy. Lasers in Surgery and Medicine, 2008. 40(7): p. 461-467.
7. Gniadecka, M., et al., Diagnosis of basal cell carcinoma by Raman spectroscopy. Journal of Raman Spectroscopy, 1997. 28(2-3): p. 125-129.
8. Larraona-Puy, M., et al., Development of Raman microspectroscopy for automated detection and imaging of basal cell carcinoma. Journal of biomedical optics, 2009. 14(5).
9. Larraona-Puy, M., et al., Discrimination between basal cell carcinoma and hair follicles in skin tissue sections by Raman micro spectroscopy. Journal of Molecular Structure, 2011. 993(1-3): p. 57-61.
10. Almond, L. M., et al., Raman spectroscopy: a potential tool for early objective diagnosis of neoplasia in the oesophagus. Journal of Biophotonics, 2011. 4(10): p. 685-695.
11. Tollefson, M., et al., Raman spectral imaging of prostate cancer: can Raman molecular imaging be used to augment standard histopathology? Bju International, 2010. 106(4): p. 484-488.
12. Haka, A. S., et al., Diagnosing breast cancer by using Raman spectroscopy. Proceedings of the National Academy of Sciences of the United States of America, 2005. 102(35): p. 12371-12376.
13. McIntosh, L. M., et al., Towards non invasive screening of skin lesions by near infrared spectroscopy. Journal of Investigative Dermatology, 2001. 116(1): p. 175-181.
14. Bird, B., et al., Infrared spectral histopathology (SHP): a novel diagnostic tool for the accurate classification of lung cancer. Laboratory Investigation, 2012. 92(9): p. 1358-1373.
15. Hutchings, J., et al., The potential for histological screening using a combination of rapid Raman mapping and principal component analysis. Journal of Biophotonics, 2009. 2(1-2): p. 91-103.
16. Rowlands, C. J., et al., Rapid acquisition of Raman spectral maps through minimal sampling: applications in tissue imaging. Journal of Biophotonics, 2012. 5(3): p. 220-229.
17. Begin, S., et al., Coherent anti Stokes Raman scattering hyperspectral tissue imaging with a wavelength swept system. Biomedical optics express, 2011. 2(5): p. 1296-306.
18. Saar, B. G., et al., Video Rate Molecular Imaging in Vivo with Stimulated Raman Scattering. Science, 2010. 330 (6009): p. 1368-1370.
19. Tu, A. T., Raman Spectroscopy in Biology: Principles and Applications. 1982: Wiley-Blackwell.
20. Movasaghi, Z., S. Rehman, and I. U. Rehman, Raman spectroscopy of biological tissues. Applied Spectroscopy Reviews, 2007. 42(5): p. 493-541.
21. Okuno, M. and H. Do. Hamaguchi, Multifocus confocal Raman microspectroscopy for fast multimode vibrational imaging of living cells. Optics Letters, 2010. 35(24): p. 4096-4098.
22. Wartewing, S., IR and Raman Spectroscopy: Fundamental Processing. 2003: Wiley-VCH.
23. Pirzer, M., Method and Device for Correcting a spectrum, in U.S. Pat. No. 7,359,815.
24. Duda, R., P. Hart, and D. Stork, Pattern Classification, 2nd Edition. 2001: Wiley & Sons, Inc.
25. Ly, E., et al., Differential diagnosis of cutaneous carcinomas by infrared spectral micro-imaging combined with pattern recognition. Analyst, 2009. 134(6): p. 1208-1214.
26. Sebiskveradze, D., et al., Automation of an algorithm based on fuzzy clustering for analyzing tumoral heterogeneity in human skin carcinoma tissue sections. Laboratory Investigation, 2011. 91(5): p. 799-811.
27. O'Callaghan, R. J. and D. R. Bull, Combined morphological spectral unsupervised image segmentation. IEEE Transactions on Image Processing, 2005. 14(1): p. 49-62.
28. Naidu, V. Multi modal image segmentation. 2010; Available from: http://www.mathworks.com/matlabcentral/fileexchange/28418-multi-modal-image-segmentation.
29. Lin, K., W. Zheng and Z. Huang, Integrated autofluorescence endoscopic imaging and point-wise spectroscopy for real-time in vivo tissue measurements. JBO Letters Vol. 15(4) 2010, 040507, 2010.
30. Bergholt, M. S. et al, Combining near-infrared-excited autofluorescence and Raman spectroscopy improves in vivo diagnosis of gastric cancer, Biosensors and Bioelectronics, 26 (2011) 4104-4110.

The invention claimed is:
1. A method of automatically identifying tissue structures in a sample, the method comprising the steps of:
   measuring a response of an area of the sample to illumination with light, wherein the sample has a sample area of 1 mm$^2$ or greater;
   identifying regions within the area via unsupervised, automated determination, wherein the identified regions are dependent upon having a measured response within a predetermined range;
   generating a spatial correlation map of the sample from the identified regions, the spatial correlation map comprising a plurality of segments;

determining one or more locations within each of the identified regions to establish a sampling pattern for spectroscopic analysis of each segment of the spatial correlation map;

performing spectroscopic analysis of the sample at the one or more determined locations to obtain 1000 or fewer spectra for the sample;

identifying a tissue structure for each region from the spectroscopic analysis performed on one or more locations therein;

producing a coloured image of the sample area specific to the tissue structure identified; and classifying each segment of the spatial correlation map according to the spectroscopic analysis.

2. The method of claim 1 wherein the spectroscopic analysis is performed using vibrational spectroscopy.

3. The method of claim 2 wherein the spectroscopic analysis is Raman spectroscopy.

4. The method of claim 1 wherein the light the sample is illuminated with is ultraviolet light.

5. The method of claim 1 wherein the measured response is a measured value of fluorescence.

6. The method of claim 5 wherein the measured fluorescence value is a measure of intensity.

7. The method of claim 6 wherein the identified regions have a measured fluorescence value greater than or less than a predetermined threshold value.

8. The method of claim 5 wherein the measured fluorescence value is a measure of fluorescence lifetime.

9. The method of claim 1 wherein the regions identified within the area have a minimum predetermined size.

10. The method of claim 9 wherein the minimum predetermined size is a region having a linear extent of greater than around 100 µm, 50 µm, 20 µm or 10 µm, or a region having an area of greater than around 0.01 mm$^2$, 0.0025 mm$^2$, 0.0004 mm$^2$ or 0.0001 mm$^2$.

11. The method of claim 1 wherein a particular tissue structure is identified for each region based on matching a spectrum from spectroscopic analysis of one or more locations within each region from a database of spectra for different tissue structures.

12. The method of claim 11 wherein the different tissue structures include a tumour.

13. The method of claim 12 wherein the different tissue structures include a basal cell carcinoma.

14. The method of claim 1 wherein a number of locations are identified within each region dependent on its size.

15. The method of claim 14 wherein two or more locations are identified within each region.

16. The method of claim 15 wherein one of the identified regions is identified as a particular tissue structure if two or more spectra from spectroscopic analysis taken at locations within the one of the identified regions indicate the same particular tissue structure.

17. The method of claim 16 wherein the particular tissue structure is a basal cell carcinoma or another type of tumour.

18. The method of claim 15 wherein one of the identified regions is identified as a particular tissue structure if a majority of spectra from spectroscopic analysis at locations within the one of the identified regions indicate the particular tissue structure.

19. The method of claim 1 wherein the locations identified within each region are at least a predetermined distance away from an outer edge of each region.

20. The method of claim 19 wherein the predetermined distance is 10 µm, 20 µm or 50 µm.

21. The method of claim 1 wherein each region is identified as dermis, epidermis, basal cell carcinoma or another tissue structure.

22. The method of claim 1 wherein 500 or fewer locations are determined within each of the identified regions.

23. The method of claim 1 wherein 100 or fewer locations are determined within each of the identified regions.

24. An apparatus for automatically identifying tissue structures in a sample, the apparatus comprising:
a sample stage for receiving a sample to be analysed;
a first light source for selectively illuminating an area of the sample;
a first detector for receiving light from the sample upon illumination by the first light source;
a second light source for selectively illuminating a location within the area of the sample; and
a spectral analyser for receiving light from the location within the area of the sample upon illumination by the second light source,
the apparatus being configured to perform a method according to claim 1.

25. A computer program product comprising a non-transitory computer-usable medium having computer-readable program code embodied therein, the computer-readable program code adapted to cause the computer to:
measure a response of an area of a sample to illumination with light, wherein the sample has a sample area of 1 mm$^2$ or greater;
identify regions within the area via unsupervised, automated determination wherein the identified regions are dependent upon having a measured response within a predetermined range;
generate a spatial correlation map of the sample from the identified regions, the spatial correlation map comprising a plurality of segments;
determine one or more locations within each of the identified regions to establish a sampling pattern for spectroscopic analysis of each segment of the spatial correlation map;
perform spectroscopic analysis of the sample at the one or more determined locations to obtain 1000 or fewer spectra for the sample;
identify a tissue structure for each region from the spectroscopic analysis performed on one or more locations therein;
produce a coloured image of the sample area specific to the tissue structure identified; and
classify each segment of the spatial correlation map according to the spectroscopic analysis.

* * * * *